United States Patent
Fung et al.

(10) Patent No.: US 6,759,236 B1
(45) Date of Patent: Jul. 6, 2004

(54) METHODS TO ENHANCE AND CONFINE EXPRESSION OF GENES

(75) Inventors: Yuen Kai Fung, Los Angeles, CA (US); Charles Gomer, Glendora, CA (US); Anne T'Ang, Los Angeles, CA (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 09/376,774

(22) Filed: Aug. 17, 1999

Related U.S. Application Data

(60) Provisional application No. 60/096,947, filed on Aug. 18, 1998, now abandoned.

(51) Int. Cl.$^7$ .................... C12N 15/00; C12N 15/64; C12Q 1/68; C12P 19/34; C07H 21/04
(52) U.S. Cl. .................. 435/320.1; 435/6; 435/91.1; 435/91.4; 536/23.1; 536/24.5
(58) Field of Search .................... 435/6, 91.1, 455, 435/468, 375, 91.4, 91.41, 320.1; 514/44; 935/33, 36; 536/23.1, 24.5

(56) References Cited

U.S. PATENT DOCUMENTS 5,965,440 A * 10/1999 Reeves ..................... 435/456
6,072,102 A *  6/2000 Cigan et al. ................ 800/265

OTHER PUBLICATIONS

US 6,124,129, 9/2000, Szafranski et al. (withdrawn)*
Voellmy et al. Proc. Batl. Aced. Sci. vol. 82, pp. 4949–4953, 1985.*
Branch, A.D. Trends in Biochem. Sci. vol. 23, pabes 45–50, 1998.*
Crooke, S.T. Antisense Research and Application, Chapter 1, pp. 1–50. Published by Springer–Verlag, 1998.*
Schofield et al. Brit. Med. Bull. vol. 51, No. 1, pp. 56–71, 1995.*
Verma et al. Nature, vol. 389, pp. 239–242, 1997.*
Friedmann, T. Scientific American, Jun. Volume, pp. 96–101, 1997.*
Crystal, R.G. Science, vol. 270, pp. 404–410, 1995.*

* cited by examiner

*Primary Examiner*—Ram R. Shukla
*Assistant Examiner*—Jane Zara
(74) *Attorney, Agent, or Firm*—Benjamin Aaron Adler

(57) ABSTRACT

The present invention provides a novel approach to gene therapy of restricted areas such as tumors. The methods introduced here comprise: (a) placing a gene of interest in a plasmid vector driven by a heat or light inducible promoter; (b) modifying this vector by including a tetracycline responsive fusion protein which acts as a transcriptional activator, thus permitting regulation of gene expression by varying the levels of drug and; (c) modifying this vector by including DNA sequences that reduce or eliminate expression of genes in normal bystander cells. Also provided are a set of vectors for both sustained and regulable expression. There is also presented novel vectors for the gene therapy treatment of local and metastatic breast, ovarian and prostate cancer.

2 Claims, 10 Drawing Sheets

METHODS TO ENHANCE AND CONFINE EXPRESSION OF GENES

CROSS-REFERENCE TO RELATED APPLICATIONS

This application claims benefit of priority of U.S. provisional application Serial No. 60/096,947, filed Aug. 18, 1998, now abandoned.

BACKGROUND OF THE INVENTION

1. Field of the Invention

The present invention relates generally to the field of gene therapy for cancer. More specifically, the present invention presents a method of controlling the expression of therapeutically valuable gene products via inducible promoters. The present invention provides a method whereby induced gene expression in the intended cell targets is enhanced and prolonged in a spatially and temporally regulable manner by means of heat or light inducible promoters. Moreover, the present invention provides a method whereby the background gene expression in non-targeted cells is reduced or eliminated.

2. Description of the Related Art

One of the major obstacles to the success of chemotherapy and radiation therapy for cancer is the difficulty in achieving tumor-specific cell killing. The inability of radiation or cytotoxic chemotherapeutic agents to distinguish between tumor cells and normal cells necessarily limits the dosage that can be applied. As a result, diseases relapse due to residual surviving tumor cells is frequently observed.

The use of gene therapy in cancer treatment presents many of the same disadvantages as chemotherapy and radiation therapy. Problems with current state-of-the-art gene therapy strategies include the inability to deliver the therapeutic gene specifically to the target cells. This leads to toxicity in cells that are not the intended targets. For example, manipulation of the p53 gene suppresses the growth of both tumor cells and normal cells, and intravenous administration of tumor necrosis factor alpha (TNFα) induces systemic toxicity with such clinical manifestations as fever and hypertension.

Attempts have been made to overcome these problems. These include such strategies as: the use of tissue-specific receptors to direct the genes to the desired tissues (Kasahara, N., et al., *Science*, 266:1373–1376 (1994)), the use of tissue-specific promoters to limit gene expression to specific tissues (e.g. use of the prostate specific antigen promoter) and the use of heat (Voellmy R., et al., *Proc. Natl. Acad. Sci. USA*, 82:4949–4953 (1985)) or ionizing radiation inducible enhancers and promoters (Trainman, R. H., et al., *Cell* 46: 567–574 (1986); Prowess, R., et al., *Proc. Natl. Acad. Sci. USA* 85, 7206–7210 (1988)) to enhance expression of the therapeutic gene in a temporally and spatially controlled manner. The heat inducible heat shock protein (HSP) promoter has been used to direct the expression of genes such as the cytokine IL-2.

Weichselbaum and colleagues were the first to discover the radiation inducible response of the early growth response (Egr-1) gene promoter. Accordingly, they have attempted to direct expression of such cytotoxic genes as TNF-α to tumor cells to enhance radiation cell killing by means of this promoter. Previously, systemic administration of the cytokine TNF-α as an adjuvant to ionizing radiation was initially reported to result in enhanced killing in a mouse xenograft tumor system. It has since been shown partially effective in human tumors. The effect of TNFα appears to be dosage-dependent, as its tumor-killing effect correlates with its serum concentration. However, systemic toxicity of TNFα restricts the dosage that can be applied and thus limits the usefulness of the treatment regimen. Attempts have also been made to deliver the TNFα gene to tumor cells via adenoviral vector and/or liposomes. Unfortunately, expression of the TNFα gene is not restricted to the tumor sites due to the 'leakiness' of the promoter.

In an attempt to localize the level of TNFα to the general area of radiation exposure and thereby reduce systemic toxicity, Weichselbaum and colleagues employed the radiation inducible Egr-1 promoter to activate the TNFα gene in situ. Earlier studies showed that the expression of certain immediate-early genes such as jun/fos and Egr-1 are activated in cells exposed to ionizing radiation (Sherman, M. L., et al., *Proc. Natl. Acad. Sci. USA*, 87: 5663–5666 (1997); Hallahan, D. E., et al., *Proc. Natl. Acad. Sci. USA*, 88: 2156–2160 (1991)). By placing the TNFα gene under the control of the Egr1 promoter (EGRp), the expression of the TNFα is enhanced in those cells harboring an EGRp-TNFα plasmid when exposed to ionizing radiation. In vivo, the serum level of TNFα is greatly enhanced (Weichselbaum R. R., et al., *Cancer Res.* 54: 4266–4269 (1994)) within a few hours after irradiation. The combined treatment with this plasmid and radiation leads to a partial regression of a xenografted tumor during the course of the treatment. The level of TNFα dropped precipitously within 24 hours; further decreases in serum level of TNFα coincided with regrowth of the tumors.

There are several possible reasons for the recurrence of the tumor upon cessation of therapy. The most obvious reason is probably the same limitation seen with chemotherapy or radiation therapy in general, viz., insufficient dosage levels. A major problem, which limits the amount of TNFα produced, is the weak and transient nature of the Egr-1 promoter. This promoter is intrinsically weak, with a maximum of less than three-fold increase in expression upon induction. Moreover, the induced expression is of necessity transient. This, coupled with the weakness of the promoter, permits only a brief exposure of the tumor cells to the TNFα.

Another factor that limits the production of sufficient dosage of TNFα is that not every tumor cell will have taken up the TNFα plasmid. While it has been suggested that repeated administration may help to improve the treatment outcome, it is not clear if the repeated delivery of a suboptimal low dosage of TNFα will be useful, the problems posed by an immune response notwithstanding. Although it might be conceivable to deliver larger doses of plasmids, the problem of promoter leakiness has hindered such an approach. It is known that a substantial basal level of activity (20–30%) can be detected with the Egr-1 promoter even in the absence of ionizing radiation (Weichselbaum, et al., supra). This is not surprising, as the radiation response element, a CArG box, is part of the serum response element.

The HSP promoter is also rather leaky. In the absence of heat, this promoter exhibits a 25–30% background level of expression, not suitable for most cytotoxic genes. As this level of expression will be harmful to unirradiated normal cells that take up the gene. Hence, administration of this plasmid has been restricted to small doses of intra-tumoral injections to minimize systemic toxicity.

Therefore, while it may be advantageous to employ a spatially and temporally regulated promoter such as the HSP and Egr-1 promoters to enhance specificity of gene expression at the site of heat or radiation treatment, current versions of those promoters have serious problems that restrict their applicability. In order to apply these promoters for use in cancer therapy, it is necessary to eliminate or greatly reduce background expression in unheated or unirradiated cells. Ideally, the expression of cytotoxic genes should be limited to the area of external stimuli (heat or radiation). Additionally, to ensure a sufficient level of expression of therapeutic genes, the weak and transient nature of gene expression driven by these promoters must be improved.

It is important to note that even when an improved inducible vector system which can restrict the expression of a therapeutic gene to the area of external stimuli is developed, there is still the problem of expression in normal heated or irradiated bystander cells. Thus, it is critical to be able to further restrict the expression of therapeutic genes only to the intended targets, e.g., tumor cells.

The prior art is deficient in the lack of effective means of inhibiting unwanted toxic side effects of gene therapy treatments for cancer, as well as providing a method for enhancing and sustaining gene expression in targeted tumor cells in a controllable manner. The present invention fulfills this longstanding need and desire in the art.

SUMMARY OF THE INVENTION

The current invention provides the composition and methods for the controlled activation of DNA molecules for gene therapy. Activation of these DNA molecules leads to the production of protein products which then may provide opportunities for therapeutic manipulation of cells containing said DNA molecules. This may be achieved via alterations in cell growth and metabolism of the targeted cells and may include effects on neighboring cells via secretion of therapeutic products. The invention offers the options of sustained activation or activation regulable by the application of antibiotics. The invention further provides novel expression vectors for use in gene therapy of local and metastatic breast, ovarian and prostate cancer.

An original strategy to confine and enhance therapeutic gene expression to tumors spatially and temporally is also presented, in the form of an expression vector designed for use in local and metastatic breast, ovarian and prostate cancer.

In one embodiment of the present invention, there is provided a method for sustained and enhanced expression of a gene via activation of a heat or light inducible promoter. In a modification of this method, heat or light is used to activate the promoter, but continued levels of gene expression are modulated by concentrations of an antibiotic (tetracycline or its derivatives), acting on a fusion protein with a tetracycline-responsive element.

In yet another embodiment of the present invention, there is provided a method of constructing the vectors for gene therapy activation modalities.

In another embodiment of the present invention, there are provided improved vectors for reducing background expression in unheated and unirradiated cells.

In another embodiment of the present invention, there are provided improved vectors for reducing expression in heated and irradiated normal bystander cells.

In another embodiment of the present invention, there are provided expression vectors for use in gene therapy treatment of local and metastatic breast and ovarian cancer.

In another embodiment of the present invention, there are provided expression vectors for use in gene therapy treatment of local and metastatic prostate cancer.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 6 illustrates the leakiness of the HSP promoter. It summarizes the results of testing the heat inducible system containing the hsp70 promoter in the expression of therapeutic genes, p53 and TNFα.

DETAILED DESCRIPTION OF THE INVENTION

Figure 1:
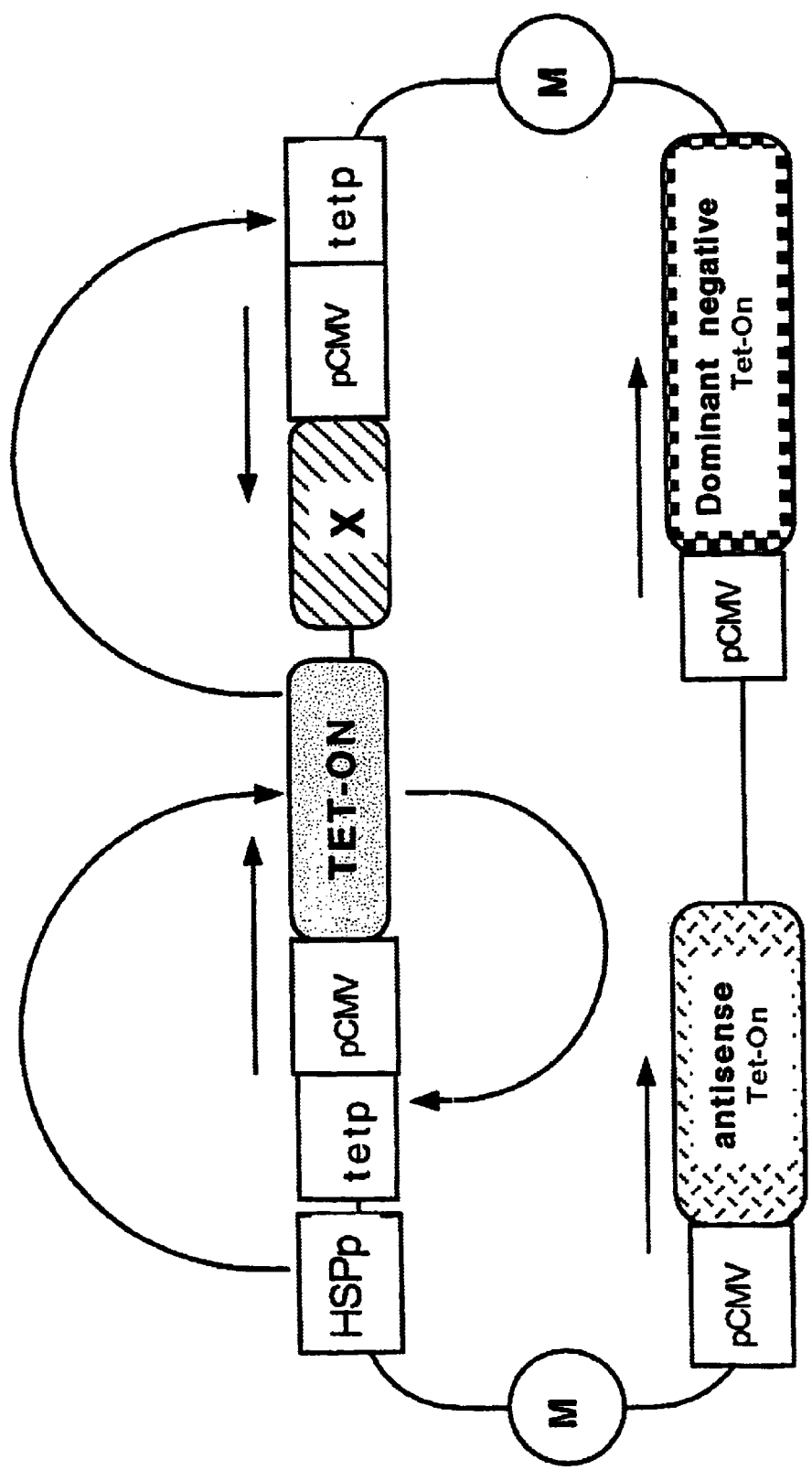
FIG. 1 shows a schematic representation of the plasmid, pDATH-X (Dominant negative, Antisense, TET-ON controllable Heat shock promoter plasmid)-p53, which consists of four cassettes as follows. (1) TET-ON is a fusion of the coding sequences for amino acids 1–207 of the tetracycline (tet) repressor and the C-terminus last 130 amino acid transcription activation domain of the VP16 protein of the herpes simplex virus (Gossen M., et al., Science, 268:1766–1769 (1995)). In Cassette 1, the TET-ON sequence is placed under the control of the HSP and the tet operator binding site and pCMV. (2) HSP is the heat shock promoter consisting of the heat shock response element (−260 to 30) of the human heat shock 70 gene promoter (Voellmy R., et al., Proc. Natl. Acad. Sci. USA 82: 4949–4953 (1985)) linked to the minimal CMV promoter, pCMV (Gossen M., et al., Science, 268:1766–1769 (1995)). In cassette 2, the therapeutic gene, X, is placed under the control of the tetp-pCMV promoter. (3) tetp is the tet operator consisting of the 19 base pair (bp) inverted repeats of the operator O2 of TN10 (Gossen M, and Bujard H., Proc. Natl. Acad. Sci. USA 89:5547–5551 (1992)) to which the tet repressor and TET-ON bind. In cassette 3, antisense TET-ON is placed under the control of the pCMV promoter. (4) Antisense TET-ON is an antisense sequence consisting of the complementary sequence to the first 80 bases of the TET-ON sequence including the ATG. In cassette 4, dominant negative TET-ON is placed under the control of the pCMV promoter. The Dominant negative TET-ON consists of the tet-repressor but without the VP16 transactivation domain, and it is placed under the control of the pCMV promoter. In the absence of heat or light, a background level of expression of the TET-ON sequence will result due to the leakiness of the minimal promoter pCMV.

As used herein, the term "heat" is to mean heat energy generated by any means, including microwaves.

As used herein, the term "light" is to mean light energy with frequencies in the visible as well as the invisible spectrum, including ionizing radiation generated by any means. This would include a radiation source such as radionuclides capable of emitting gammma and or beta particles, or by a linear accelerator.

In accordance with the present invention, there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

The present invention is directed towards a new method of gene therapy for confined areas such as tumors. In accordance with the above-mentioned object there is provided a mechanism for both constitutively active and regulable gene expression via plasmids containing elements which are heat and or light activated and responsive to presence and concentration of antibiotic (tetracycline and its derivatives). In regulating gene expression, heat or light initiates the expression, but the gene is constitutively expressed only in the presence of the antibiotic (tetracycline and its derivatives). Concentration of the antibiotic controls the level and duration of the gene expression.

For the confinement of gene expression to tumor cells, there are provided two mechanisms for the suppression of gene expression in normal cells that are bystander targets of heat or radiation. In the instance of normal cells not exposed to heat or light, which inadvertently take up the plasmid, expression of the therapeutic gene due to background activity of the promoter is suppressed by the constitutive expression of antisense and dominant negative DNA sequences to the heat or light inducible, antibiotic dependent transcriptional activator built into the plasmid. In the instance whereby normal cells that take up the plasmid are then exposed to heat or light, there is an additional mechanism for preventing the expression of the therapeutic gene. This is achieved by the use of a modified 'two hybrid' system where the antibiotic dependent transcriptional activator is itself under the control of both the expression of tissue-specific transcriptional activators and the exposure to heat or light. Expression of the therapeutic gene is therefore found only in cells that have been both exposed to heat or light and that express tissue-specific transcription factors.

In one embodiment of the present invention, there is provided a recombinant vector, pDATH-X (Dominant negative, Antisense, TET-ON controllable Heat shock promoter plasmid), for the purpose of reducing background levels of expression. This vector is comprised of the cassettes: (a) a fusion of the coding sequences for amino acids 1–207 of the tetracycline repressor and the C-terminus last 130 amino acid transcription activation domain of the VP16 protein of the herpes simplex virus; (b) a heat shock promoter consisting of heat shock response elements (−260 to 30) of the human heat shock 70 gene promoter linked to the minimal cytomegalovirus promoter, pCMV; (c) a tet operator consisting of the 19 bp inverted repeats of the operator O2 of TN10 to which the tet repressor and TET-ON bind; and (d) an antisense sequence consisting of the complementary sequence to the first 80 bases of the TET-ON sequence including the ATG.

In another embodiment of the present invention provides a method of achieving sustained expression of a gene under control of a heat or light inducible promoter, comprising the step of: introducing the vector containing said gene into the host organism; and applying heat or light energy. In another embodiment of the invention, said host organism is a human.

In yet another embodiment of the invention, there is provided a recombinant vector, pDATE-X (Dominant negative, Antisense, TET-ON controllable EGR promoter expression plasmid), said vector comprising the cassettes: (a) in cassette 1, the TET-ON sequence is placed under the control of the EGRp, the tetracycline operator binding site and pCMV; (b) in cassette 2, the therapeutic gene X, is placed under the control of the tetp-pCMV promoter; (c) in cassette 3, antisense TET-ON is placed under the control of the pCMV promoter; and (d) in cassette 4, dominant negative TET-ON is placed under the control of the pCMV promoter.

Another embodiment of the present invention provides a recombinant vector, pRIBs-X, (Radiation-Inducible, Breast-specific Promoter) expression vector, said vector comprising the cassettes: (a) cassette 1 contains "Gal-DBD-mx" which is a fusion open reading frame encoding the N-terminus (amino acids 1–147) DNA-binding domain of the yeast GAL4 protein (Gal-DBD) fused to the basic helix-loop-helix-leucine zipper domain of Max (amino acids 8–112) followed by SV40 poly A- the resulting fusion gene GAL-DBD-mx is controlled by the radiation inducible Egr-1 promoter; (b) cassette 2 is comprised of the minimal CMV promoter, "antisense Gal-DBD-mx", which is an antisense construct complementary to the Gal-DBD-mx sequence, "IRES", which is an internal ribosomal entry site and "Gal-DBD" which competes with the Gal-DBD-mx for the pGAL binding site; (c) cassette 3 is comprised of "VP16-TA-mc" which is a fusion open reading frame encoding at the N-terminus the first 11 amino acids of Gal4 (amino acids 1–147), followed by the nuclear localization signal of the SV40 large T antigen, the 130 amino acid C-terminus transactivation domain of the herpes simplex viral protein VP16, the basic helix-loop-helix-leucine zipper domain of c-Myc (amino acids 350–439), followed by SV40 polyA—the resulting fusion gene, VP16-TA-mc, placed under the control of the c-erbB2 promoter "perB2" up to the first ATG; (d) cassette 4 contains "Galp", five copies of a17-mer DNA-binding site for Gal4. The TET-ON sequence is placed under the control of the GAPp-ptet promoter and the therapeutic gene, X, is linked to the TET-IN via an IRES; (e) cassette contains an antisense TET-ON which is a sequence consisting of the complementary sequence to the first 80 bases of the TET-ON sequence including the ATG, placed under the control of the pCMV promoter; and (f) cassette 6 contains a dominant negative TET-ON consisting of the coding sequences for amino acids 1–207.

There are further provided variants of the preceding vectors, wherein the perbB2 promoter is replaced with the whey acidic protein promoter or the stromelysin 3 promoter.

Another embodiment of the invention provides a method for the treatment of local and metastatic breast and ovarian cancer comprising: administration to the patient a pRIBs-X expression vector (or a variant thereof) containing a cytotoxic gene. A representative cytotoxic gene is tumor necrosis factor alpha.

The present invention is also directed to a recombinant pRIPs-X (Radiation-Inducible, Prostate-specific Promoter) expression vector, said vector comprising the cassettes: (a) cassette 1 contains "Gal-DBD-mx" which is a fusion open reading frame encoding the N-terminus (amino acids 1–147) DNA-binding domain of the yeast GAL4 protein fused to the basic helix-loop-helix leucine zipper domain of Max (amino acids 8–112) followed by SV40 polyA—the resulting fusion gene GAL-DBD-mx is controlled by the radiation inducible Egr-1 promoter; (b) cassette 2 is comprised of the minimal CMV promoter, antisense Gal-DBD-mx, which is an antisense construct complementary to the Gal-DBD-mx sequence, IRES, which is an internal ribosomal entry site and Gal-DBD which competes with the Gal-DBD-mx for the pGAL binding site; (c) cassette 3 is comprised of "VP16-TA-mc", a fusion open reading frame encoding at the N-terminus the first 11 amino acids of Gal4, followed by the nuclear localization signal of the SV40 large T antigen, the 130 amino acid C-terminus transactivation domain of the herpes simplex viral protein VP16, the basic helix-loop-helix leucine zipper domain of c-Myc (amino acids 350–439), followed by SV40 polyA—the resulting fusion gene, VP16-TA-mc, is placed under the control of the probasin gene promoter "pProbasin" up to the first ATG; (d) cassette 4 contains GALp, five copies of the 17-mer DNA-binding site for Gal4. The TET-ON sequence is placed under the control of the GALp-ptet promoter and the therapeutic gene, X, is linked to the TET-ON via an internal ribosomal entry site; (e) cassette 5 contains an antisense TET-ON which is a sequence consisting of the complementary sequence to the first 80 bases of the TET-ON sequence including the ATG, placed under the control of the pCMV promoter; and (f) cassette 6 contains a dominant negative TET-ON consisting of the coding sequence for amino acids 1–207. A variant of the preceding vector is also contemplated, wherein the probasin promoter is replaced with the prostate specific antigen promoter.

Another embodiment of the invention provides a method for the treatment of local and metastatic prostate cancer comprising: administration to the patient a pRIPs-X expression vector (or a variant thereof) containing a cytotoxic gene. A representative cytotoxic gene is tumor necrosis factor alpha.

In yet another embodiment of the present invention, there is provided a recombinant expression vector, pHIBs-X (Heat Inducible, Breast-specific promoter), said vector comprising the cassettes: (a) cassette 1 contains Gal-DBD-mx which is a fusion open reading frame encoding the N-terminus (amino acids 1–147) DNA-binding domain of the yeast GAL4 protein fused to the basic helix-loop-helix leucine zipper domain of Max (amino acids 8–112) followed by SV40 polyA—the resulting fusion gene GAL-DBD-mx is controlled by the heat inducible heat shock protein promoter; (b) cassette 2 is comprised of the minimal CMV promoter, antisense Gal-DBD-mx, a construct complementary to the Gal-DBD-mx sequence, an internal ribosomal entry site and Gal-DBD, which competes with the Gal-DBD-mx for the pGAL binding site; (c) cassette 3 is comprised of "VP16-TA-mc" which is a fusion open reading frame encoding at the N-terminus the first 11 amino acids (amino acids 1–147), followed by the nuclear localization signal of the SV40 large T antigen, the 130 amino acid C-terminus transactivation domain of the herpes simplex viral protein VP16, the basic helix-loop-helix leucine zipper domain of c-Myc (amino acids 350–439), followed by SV40 polyA—the resulting fusion gene VP16-TA-mc is placed under the control of the c-erbB2 gene promoter "perbB2" up to the first ATG; (d) cassette 4 contains GALp, five copies of a 17-mer DNA-binding site for Gal4. The TET-ON sequence is placed under the control of the GALp-ptet promoter and the therapeutic gene, X, is linked to the TET-ON via an internal ribosomal entry site; (e) cassette 5 contains an antisense TET-ON which is a sequence consisting of the complementary sequence to the first 80 bases of the TET-ON sequence including the ATG, placed under the control of the pCMV promoter; and (f) cassette 6 contains a dominant negative TET-ON consisting of the coding sequences for amino acids 1–207. Variants of the preceding vector are contemplated, wherein the perbB2 promoter is replaced with the whey acidic protein promoter or the stromelysin 3 promoter.

The present invention is further directed to a method for the treatment of local and metastatic breast and ovarian cancer comprising: administration to the patient a pHIBs-X expression vector (or a variant thereof) containing a therapeutic gene. A representative therapeutic gene is tumor necrosis factor alpha.

Another embodiment of the invention provides a recombinant vector, pHIPs-X (Heat-Inducible, Prostate-specific Promoter), said vector comprising the cassettes: (a) cassette 1 contains Gal-DBD-mx which is a fusion open reading frame encoding the N-terminus (amino acids 1–147) DNA-binding domain of the yeast GAL4 protein fused to the basic helix-loop-helix leucine zipper domain of Max (amino acids 8–112) followed by SV40 polyA—the resulting fusion gene GAL-DBD-mx is controlled by the heat inducible heat shock protein promoter; (b) cassette 2 is comprised of the minimal CMV promoter (mCMVp), antisense Gal-DBD-mx, a construct complementary to the Gal-DBD-mx sequence, an internal ribosomal entry site and Gal-DBD, which competes with the Gal-DBD-mx for the pGAL binding site; (c) cassette 3 is comprised of "VP16-TA-mc", a fusion open reading frame encoding at the N-terminus the first 11 amino acids of Gal4, followed by the nuclear localization signal of the SV40 large T antigen, the 130 amino acid C-terminus transactivation domain of the herpes simplex viral protein VP16, the basic helix-loop-helix leucine zipper domain of c-Myc (amino acids 350–439), followed by SV40 polyA—the resulting fusion gene, VP16-TA-mc, is placed under the control of the probasin gene promoter "pProbasin" up to the first ATG; (d) cassette 4 contains GALp, five copies of a 17-mer DNA-binding site for Gal4. The TET-ON sequence is placed under the control of the GALp-ptet promoter and the therapeutic gene, X, is linked to the TET-ON via an internal ribosomal entry site; (e) cassette 5 contains an antisense TET-ON which is a sequence consisting of the complementary sequence to the first 80 bases of the TET-ON sequence including the ATG, placed under the control of the pCMV promoter; and (f) cassette 6 contains a dominant negative TET-ON consisting of the coding sequences for amino acids 1–207. A variant of the preceding vector is contemplated, wherein the probasin promoter is replaced with the prostate-specific antigen promoter.

In another embodiment of the invention, there is provided a method for the treatment of local and metastatic prostate cancer comprising: administration to the patient a pHIPs-X vector (or a variant thereof) containing a therapeutic gene. representative therapeutic gene is tumor necrosis alpha.

It is specifically contemplated that pharmaceutical compositions of the present invention may be prepared for the purpose of gene therapy. In such a case, the composition comprises a vector of the present invention and a pharmaceutically acceptable carrier. A person having ordinary skill in the art of cancer chemotherapy would readily be able to determine, without undue experimentation, appropriate dosages and routes of administration. For gene therapy, the gene of interest contained in one of the plasmid vectors of the present invention, could be delivered to the target cell via a viral vector or liposome.

The level of ordinary skill of the average scientist in the area of molecular cancer biology has increased substantially in recent years. A person having ordinary skill in this art would readily be able to construct and utilize the plasmids for this novel approach to gene therapy given the teachings of the present specification.

The following examples are given for the purpose of illustrating various embodiments of the invention and are not meant to limit the present invention in any fashion.

EXAMPLE 1

The pDATE Vector: Structure and Mode of Action

Figure 2:
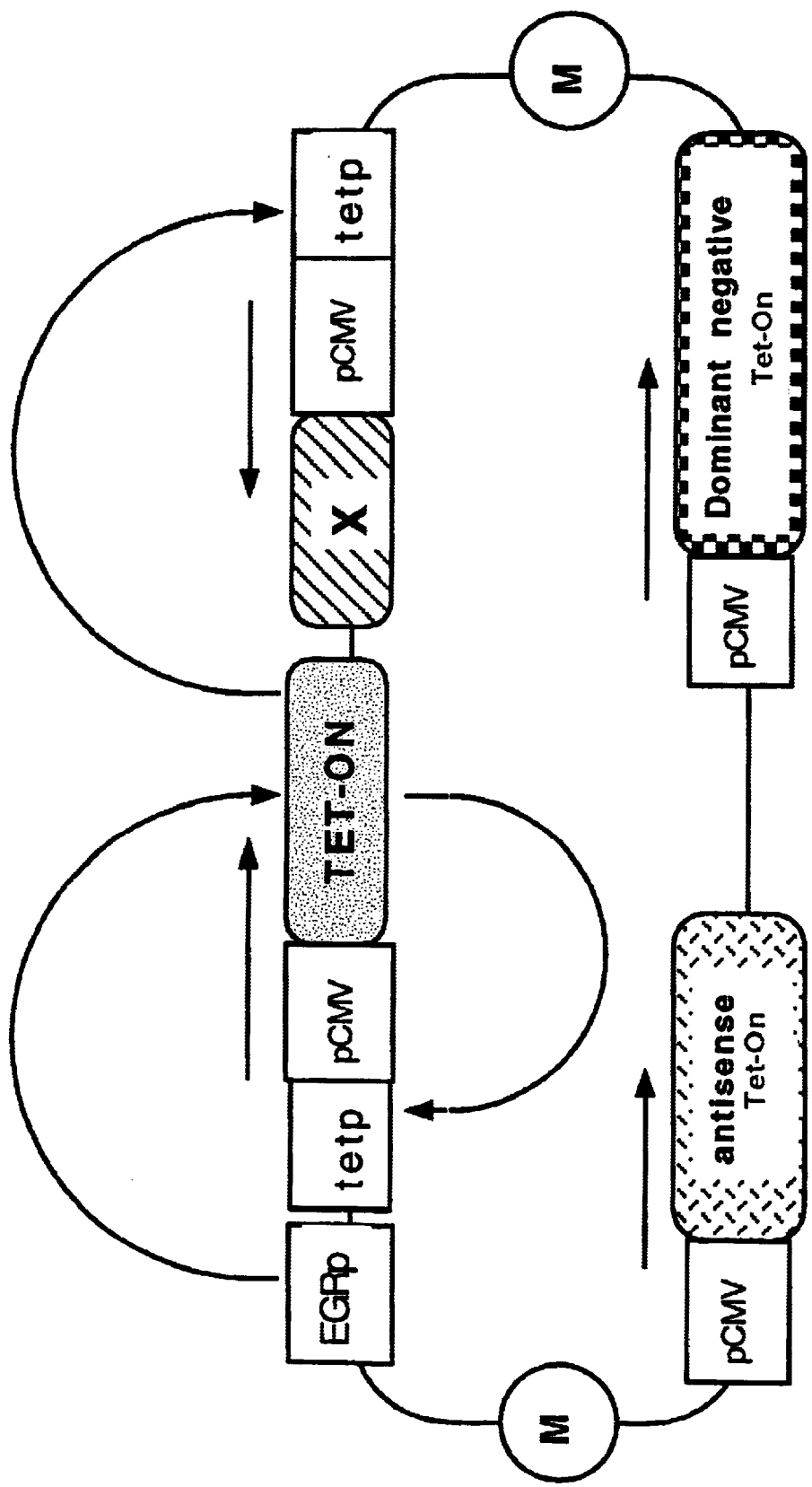
FIG. 2 depicts the pDATE vector. The plasmid, pDATE-X (Dominant negative, Antisense, TET-ON controllable EGR promoter expression plasmid) consists of four cassettes as follows: 1) in cassette 1, the TET-ON sequence is placed under the control of the EGRp, the tetracycline operator binding site and pCMV; 2) in cassette 2, the therapeutic gene, X, is placed under the control of the tetp-pCMV promoter; 3) in cassette 3, antisense TET-ON is placed under the control of the pCMV promoter; and 4) in cassette 4, dominant negative TET-ON is placed under the control of the pCMV promoter. "TET-ON" is a fusion of the coding sequences for amino acids 1–207 of the tet repressor and the C-terminus 130 amino acid transcription activation domain of the VP16 protein of the herpes simplex virus. "EGRp" is the radiation inducible promoter consisting of fragment −425 to +65 of the EGR-1 promoter containing four copies of the CArG domain. "ptet" is the tet operator consisting of the 19 bp inverted repeats of the operator O2 of TN10 to which the tet repressor and TET-ON bind, linked to the minimal CMV promoter, pCMV. "Antisense Tet-On" is a sequence consisting of the complementary sequence to the first 80 bases of the TET-ON sequence including the ATG. "Dominant negative TET-ON" consists of the coding sequences for amino acids 1–207 of the tet repressor placed under the control of the pCMV promoter. "M" is the chicken lysosomal matrix attachment site to isolate the position effects of each of the cassettes.

FIG. 2 is a schematic depiction of the pDATE vector. The pDATE-X plasmid functions via a feed-forward reaction to amplify the expression of TET-ON and X. In the absence of radiation, background expression due to leakiness of the EGRp will result in the synthesis of TET-ON mRNA. Translation of this mRNA is reduced by the concomitant expression of antisense TET-ON RNA. Moreover, leaked-through translated TET-ON protein is inactive without tetracycline. In the presence of tetracycline, the leaked (translated) TET-ON protein becomes active, but the feed-forward reaction is prevented by the constitutively expressed dominant negative TET-ON protein which competes for the same DNA binding site of the ptet promoter.

Two chicken lysosomal matrix attachment sites (MAR) are inserted to isolate the position effects of the cassettes (McKnight, R. A., et al., *Mol. Reprod. & Dev.*, 44:179–184 (1996)). While they may be unnecessary when the antisense and dominant negative TET-ON expressions are driven by the minimal CMV promoter, MARs may be needed if stronger promoters like the human β actin promoter are to drive their expression.

When cells harboring the pDATE-X are exposed to radiation, an initial burst of TET-ON transcription occurs, leading to the synthesis of 2–4-fold above background level of TET-ON in greater excess than the dominant negative TET-ON. This excess TET-ON protein, in the presence of tetracycline, then binds to the tetp promoters to which the coding sequence of both TET-ON and X are linked and engages in a feed-forward reaction. This reaction is controlled by the level of tetracycline. As such, X expression is elevated and the duration lengthened until tetracycline is removed, at which point the half-life of the TET-ON protein will determine how long the feed-forward reaction can be restarted using tetracycline without further radiation exposure.

This vector makes use of a feed-forward reaction to achieve and maintain a high level of inducible gene expression. This feed-forward feature overcomes the transient nature and weakness of the inducible promoter. When the feed-forward reaction is limited to a few hours, there is a large difference in the level of TET-ON achieved in heated and unheated cells. It is thus possible to adjust the difference in the level of amplified TET-ON in irradiated and unirradiated cells by enhancing the former with the alternate addition and removal of tetracycline. However, while the addition and removal of tetracycline can be precisely controlled in cell culture, it is difficult to do so in vivo due to the heterogeneity of tetracycline level in tissues and the variation in the absorption and removal of tetracycline in vivo in different individuals. Thus, it is critical to minimize the leak through expression of TET-ON with antisense and dominant negative cassettes so that the feed-forward reaction does not significantly amplify its level in unirradiated cells.

If necessary, the action of this vector can be further fine-tuned by replacing the pCMV minimal promoter with a much stronger promoter such as the human β actin promoter to drive the expression of the antisense and the dominant negative TET-ON. In addition, the copy numbers of the antisense and the dominant negative coding sequences can be increased.

For in vivo induction of TET-ON expression, oxytetracycline will be used because of its short in vivo half-life. In humans, after a single oral dose peak plasma concentration of oxytetracycline is reached at 2–4 hours (see, e.g., Goodman & Gilman's *The Pharmacological Basis of Therapeutics*). The level of TET-ON expression as a function of oxytetracycline concentration can thus be monitored. Oxytetracycline is short acting with an in vivo half-life of only 9 hours (versus doxycycline which has a half-life of 18 hours). At the end of 24 hours, the oxytetracycline level is reduced to <25% of input (about 10–30 % are never absorbed and are excreted in the active form).

EXAMPLE 2

The pDATH Vector: Structure and Mode of Action

FIG. 1 is a schematic depiction of the pDATH-X vector. This vector operates in identical fashion to the pDATE-X vector, except that the Egr-1 promoter is replaced with the HSP promoter and that heat is used in place of light/ionizing radiation.

EXAMPLE 3

Verification of the Concept of Amplifiable and Sustained Expression of TET-On and p53 with the Feed-forward Inducible Promoter To further validate the concept of heat inducible, tetracycline feed-forward amplification of gene expression, two plasmids were constructed. The plasmid "ptet-splice p53 wt" was constructed by subcloning a wild-type p53 cDNA into the ptet-splice vector (Gibco BRL) which places p53 under the control of the tetp promoter (consists of the regulatory sequences from the tetracycline-resistance operon upstream of a minimal hCMV promoter). The plasmid "HSP-tetp-TET-ON" was constructed by replacing the CMV promoter in ptet-on (Clontech) with 300 bp of the human heat shock protein promoter and the tetp promoter.

H358, a non-small cell lung carcinoma cell line with a homozygous deletion of p53, was grown in RPMI+10% fetal calf serum. $10^7$ exponentially growing cells were cotransfected with 50 µg of "ptet-splice p53 wt" and 10 µg of "HSP-tetp-TET-ON" by electroporation using a BRL cell-Porator at 1180 µF and 240 V in 0.8 ml RPMI+6 mM glucose. Transfected cells were plated out at 25% confluence for 36 hours and then half of them were heat-shocked at 45° C. for twenty minutes. Six hours after heat shock, cells were treated with different doses of doxycycline. At various time points after the addition of doxycycline, cells were stained immunohistochemically with the monoclonal p53 antibody DO-1 (Santa Cruz Biologicals) using an immunoperoxidase cell staining kit (Vector) and diaminobenzidine (DAB). For each point, the digital images of fifty immunostained cells were captured using a Nikon microscope. The amount of protein expressed in each cell is proportional to the intensity of staining which was expressed as I=1/T, where T is a measure of the transmitted light/unit area. Results of one such experiment at 0.01–0.1 µg/ml of doxycycline are shown in FIG. 8.

Figure 8:
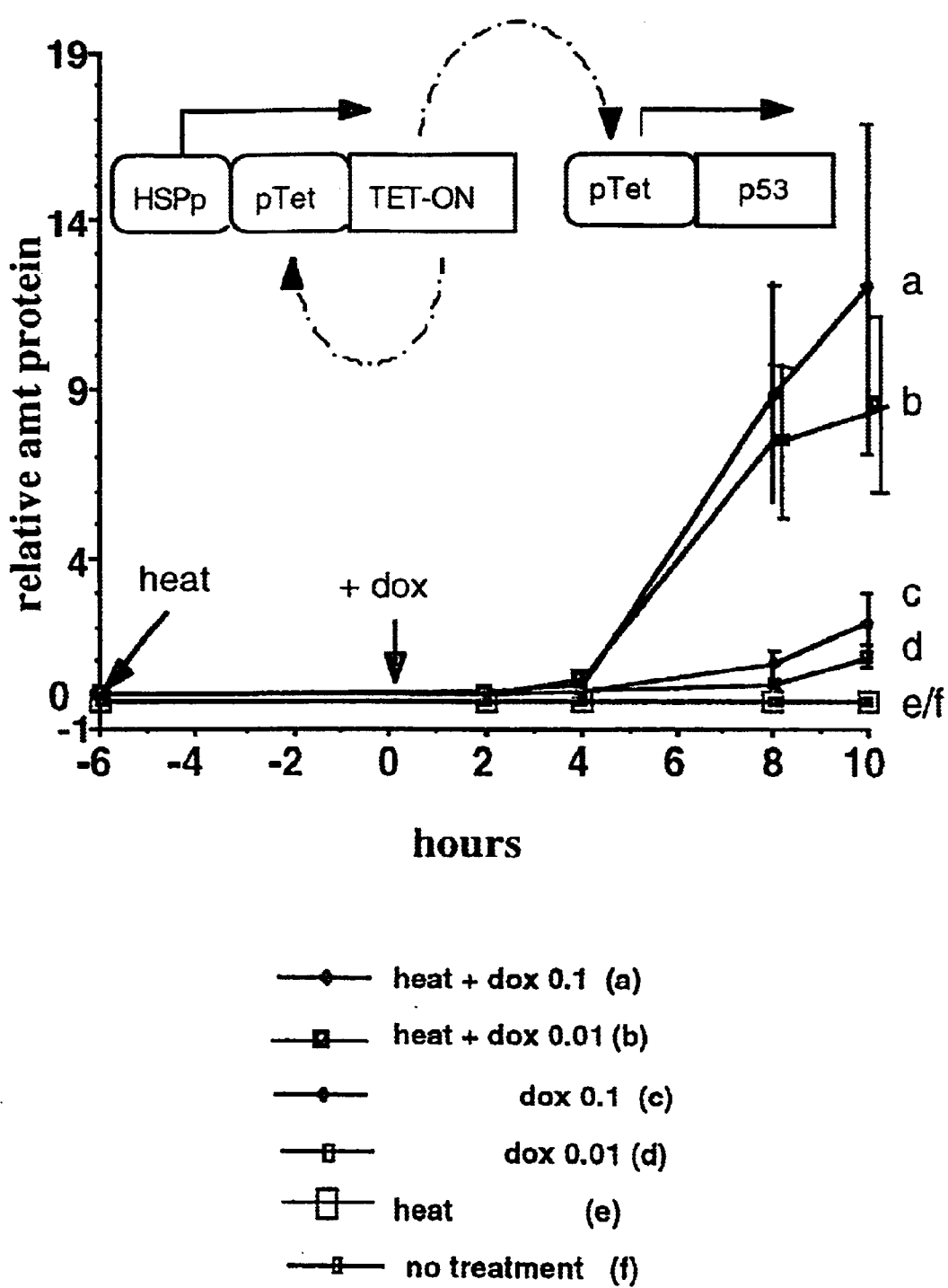
FIG. 8 shows the expression kinetics of p53 in the H358 lung carcinoma cell line by the feed-forward reaction, where a,b,c,d and e represent the levels of p53 reached at 10 hours after the feed-forward reaction. Six hours after heat shock, transfected cells were treated with different doses of doxycycline. At various time points after the addition of doxycycline, the cells were stained with a p53 antibody. For each point, the digital images of fifty immunostained cells were captured using a Nikon microscope. The amount of protein expressed in each cell is proportional to the intensity of staining, expressed as I=1/T (where T is a measure of the transmitted light/unit area. This plot shows the results of one such experiment using 0.01–0.1 µg/ml doxycycline.
Figure 9:
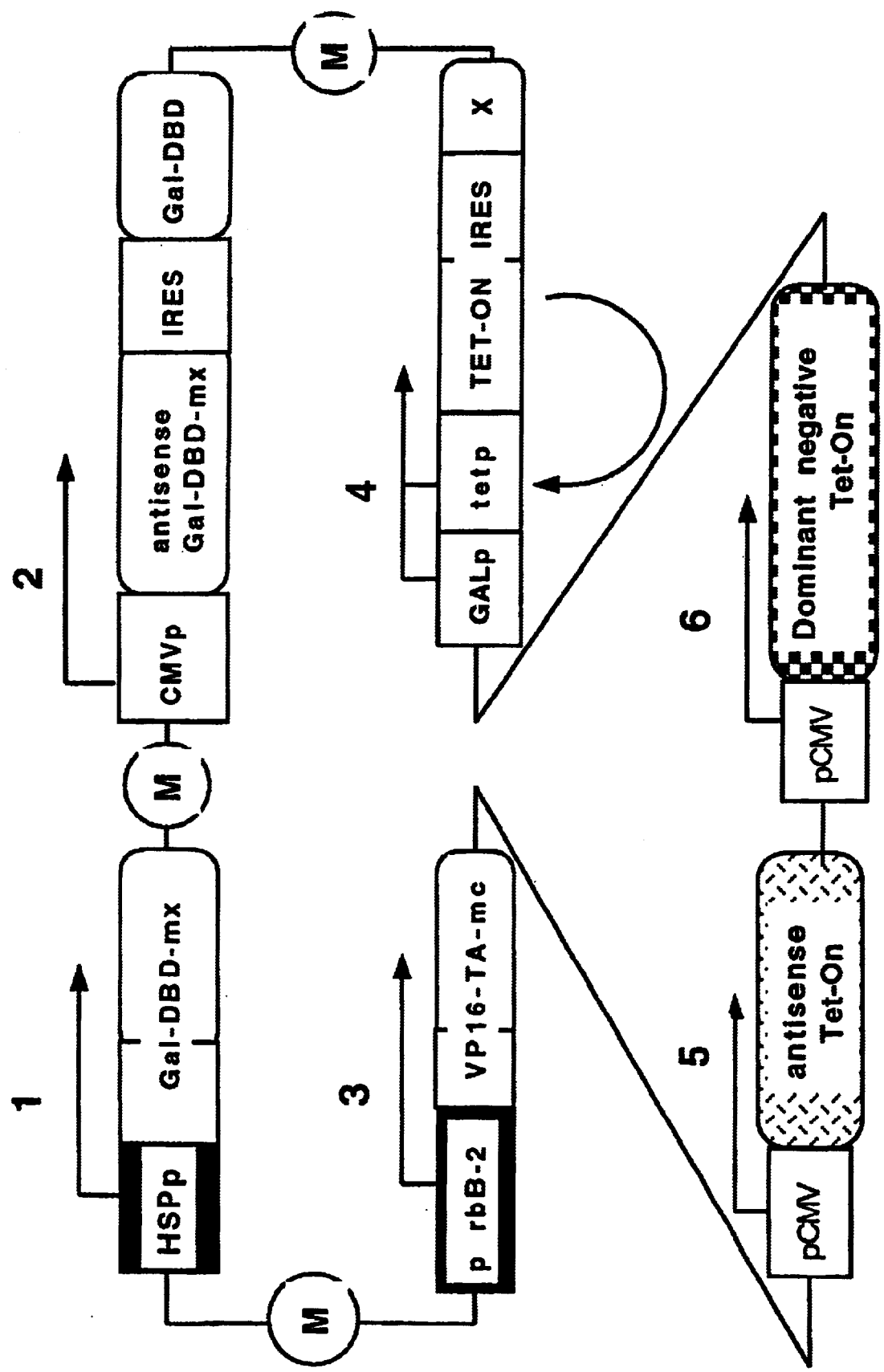
FIG. 9 depicts the pHIBS-X (Heat-Inducible, Breast-specific Promoter) expression vector. The pHIBS vector is comprised of six cassettes. Gene cassette 1 differs from the vectors described above only in that it contains "Gal-DBD-mx" which is a fusion open reading frame encoding the N-terminus (amino acids 1–147) DNA-binding domain of the yeast GAL4 protein (Gal-DBD) fused to the basis helix-loop-helix-leucine zipper (bHLHLZ) domain of Max (mx, amino acids 8–112) followed by SV40 poly A. The resulting fusion gene GAL-DBD-mx is controlled by the heat inducible HSP promoter. Gene cassette 2 is comprised of the minimal CMV promoter (mCMVp), "antisense Gal-DBD-mx", which is an antisense construct complementary to the Gal-DBD-mx sequence, "IRES", which is an internal ribosomal entry site and "Gal-DBD" which competes with the Gal-DBD-mx for the pGAL binding site. Gene cassette 3 is comprised of "VP16-TA-mc" which is a fusion open reading frame encoding at the N-terminus the first 11 amino acids of Gal4 (amino acids 1–147), followed by the nuclear localization signal of the SV40 large T antigen, the 130 amino acid C-terminus transactivation domain of the herpes simplex viral protein VP16, the bHLHLZ domain of c-Myc (amino acids 350–439), followed by SV40 polyA. The resulting fusion gene, VP-16TA-mc, is placed under the control of the c-erbB-2 promoter "perbB2" up to the first ATG. Gene cassette 4 contains "GALp", consisting of five copies of a 17-mer DNA-binding site for Gal4. The TET-ON sequence is placed under the control of the GALp-ptet promoter and the therapeutic gene, X, is linked to the TET-ON via an IRES; Gene cassette 5 contains an antisense TET-ON which is a sequence consisting of the complementary sequence to the first 80 bases of the TET-ON sequence including the ATG, placed under the control of the pCMV promoter. Gene cassette 6 contains a dominant negative TET-ON consisting of the coding sequences for amino acids 1–207 of the tet repressor placed under the control of the pCMV promoter.

When 0.1 µg/ml of doxycycline was added at 6 hours after heating (when the level of induced TET-ON should have been at its peak), more than 12 fold amplification of p53 was reached in 10 hours (curves a and b, FIG. 8). During this time, doxycycline also started a feed-forward reaction in the unheated cells as indicated by the substantial level of TET-ON. However, since the amplification started off from a lower level, the amplified level of TET-ON at 10 hours reached only a low level (curves c and d, FIG. 8).

It is possible to regulate the level of induced p53 in the feed-forward system with an alternate regimen of tetracycline addition and removal. In the time it takes for TET-ON (e.g. FIG. 8 level [c]) in the unheated cells to decline back to background level [e] after removal, the level of TET-ON in the heated cells, [a], would have declined by a similar proportion (which is equal to [c]-[e]). However, since this level ([a]-[c]-[e]) is much higher than in the unheated cells [e], the addition of tetracycline will re-start the feed-forward reaction for the heated cells from a much higher level ([a]-([c]-[e])). As such, the level of background p53 in unheated cells can be kept at or below the low level reached at 10 hours ([c]) whereas the p53 level in heated cells will continue to escalate. Thus, while the TNFα and p53 expression driven by the HSP directly is transient, the expression driven by the feed-forward system is on for as long as tetracycline is available. Since the regimen of tetracycline addition in vivo will be determined by the decay rate of tetracycline in vivo, it is important to know the half-life of the TET-ON in tumor cells.

In vivo, the pharmacokinetics of tetracycline is heterogeneous for different tissues. Preferential concentration of tetracycline in specific tissues will lead to higher background expression of TET-ON in some tissues. For example, in humans, 10–35% of oxytetracycline is removed via the kidney, a substantial amount of which is excreted in the active form. Therefore, it is desirable to minimize the background expression levels at the onset to prevent run away amplification in the unintended tissues. The pDATE and pDATH inducible systems use a constitutively expressed antisense TET-ON to suppress the background level of TET-ON translation and a dominant negative TET-ON to compete with leak-through expressed TET-ON to suppress the background expression. With the suppressed background, the timing of tetracycline addition is only affected by the desired level and duration of the expression of the therapeutic genes and not by the need to suppress the level of background expression in normal unirradiated cells.

EXAMPLE 4

Reduction in Background Levels of Expression

Employing the 300 bp HSP promoter, the background level of expression without heat or light is about 25% of the level seen with heat or light. To reduce this, the HSP was linked from −80 to +30 to the minimal pCMV promoter. The pCMV promoter is preferred due to its lower background expression. Additionally, it permits greater amplification of the expression of the therapeutic gene, independent of the constraints of the weaker HSP promoter, which is used to initiate the reaction with a burst of heat or light.

To further overcome the problem of background expression, two cassettes in the plasmid pDATH are introduced. An antisense to TET-On is placed under the control of the pCMV promoter. The constitutively produced antisense binds to any TET-On sense mRNA from the background transcription and prevents its being translated. An additional block on background transcription is provided in cassette #4 in which a dominant negative TET-On with the DNA binding site, but not the transcription activation domain, is placed under the control of the pCMV. This results in background transcription driving the production of TET-On and dominant negative TET-On, which then compete for the ptet binding site.

EXAMPLE 5

Monitoring of p53 Expression Levels

To ensure that a suitable level of antisense TET-On RNA and dominant negative TET-On protein is produced, levels of p53 expression are monitored to calibrate copy number and strength of the promoter needed in order to reduce background. First, cell lines harboring pDATH are isolated in the absence of tetracycline. The level of p53 or a cotransfected ptet-EGFP is then monitored to determine the copy number of antisense TET-On and dominant negative TET-On that needs to be incorporated into pDATH to reduce background expression.

EXAMPLE 6

The Expression Vector pRIBs for Treatment of Local and Metastatic Breast and Ovarian Cancer As mentioned supra, genes placed under the control of such promoters as the radiation inducible promoter of the Egr-1 gene are often expressed only transiently and at low levels. This renders them unsuitable for use in cancer therapy. To overcome these problems, the expression vector pRIBs-X (Radiation-Inducible, Breast-specific Promoter) was designed.

Figure 3:
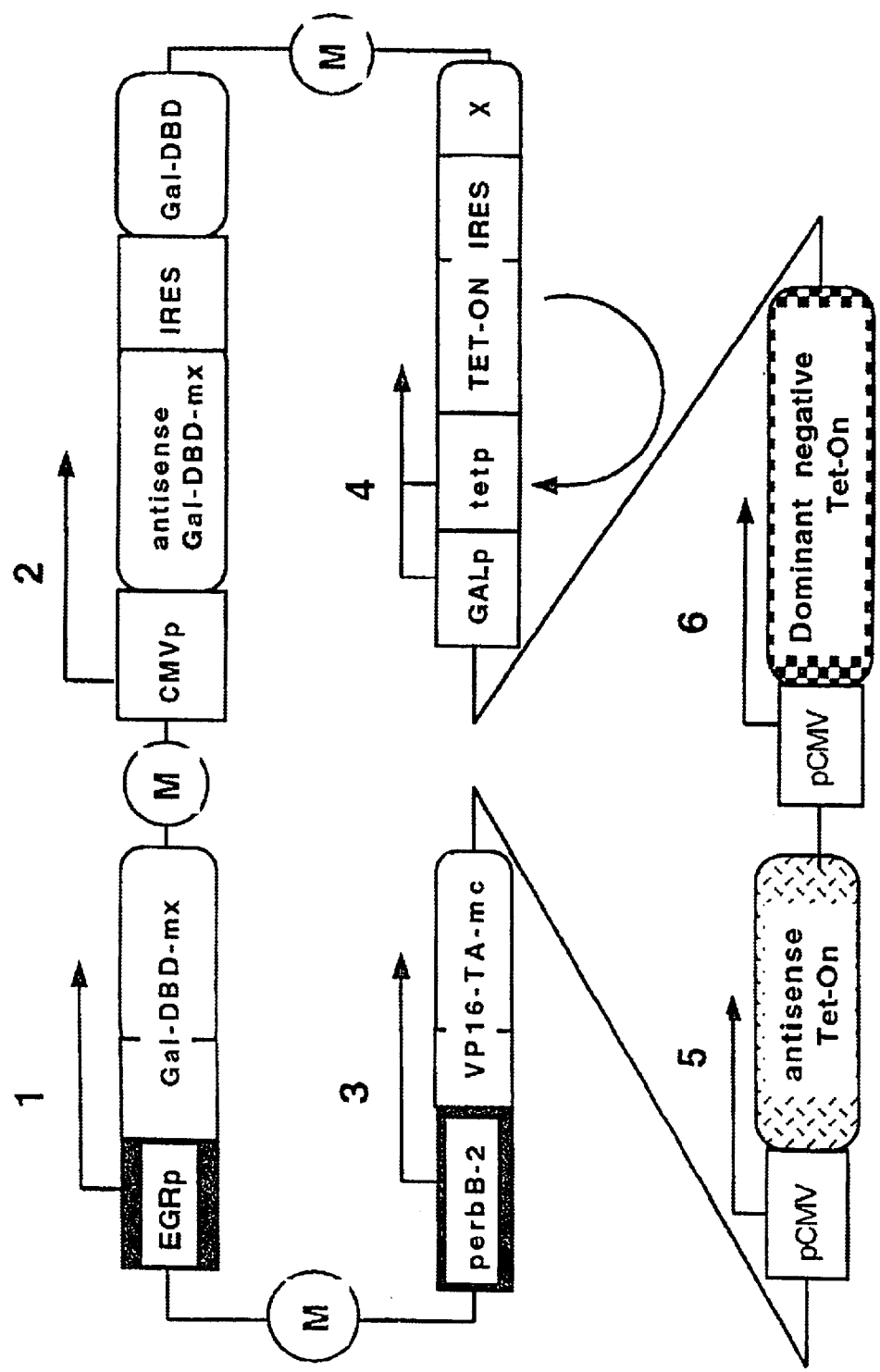
FIG. 3 depicts the structure of the pRIBs-X (Radiation-Inducible, Breast-specific Promoter) expression vector. The pRIBS vector is comprised of four cassettes. Gene cassette 1 differs from previously described vectors only in that it contains "Gal-DBD-mx" which is a fusion open reading frame (ORF) encoding the N-terminus (amino acids 1–147) DNA-binding domain of the yeast GAL4 protein (Gal-DBD) fused to the basis helix-loop-helix-leucine zipper (bHLHLZ) domain of Max (mx, amino acids 8–112) followed by SV40 poly A. Gene cassette 2 is comprised of the minimal CMV promoter (mCMVp), "antisense Gal-DBD-mx", which is an antisense construct complementary to the Gal-DBD-mx sequence, "IRES", which is an internal ribosomal entry site and "Gal-DBD" which competes with the Gal-DBD-mx for the pGAL binding site. Gene cassette 3 is comprised of "VP16-TA-mc" which is a fusion open reading frame encoding at the N-terminus the first 11 amino acids of Gal4 (amino acids 1–147), followed by the nuclear localization signal of the SV40 large T antigen, the 130 amino acid C-terminus transactivation domain of the herpes simplex viral protein VP16, the bHLHLZ domain of c-Myc (amino acids 350–439), followed by SV40 polyA. The resulting fusion gene, VP-16TA-mc, is placed under the control of the c-erbB-2 promoter "perbB2" up to the first ATG. Gene cassette 4 contains "GALp", consisting of five copies of a 17-mer DNA-binding site for Gal4. The TET-ON sequence is placed under the control of the GALp-ptet promoter and the therapeutic gene, X, is linked to the TET-ON via an IRES; Gene cassette 5 contains an antisense TET-ON which is a sequence consisting of the complementary sequence to the first 80 bases of the TET-ON sequence including the ATG, placed under the control of the pCMV promoter. Gene cassette 6 contains a dominant negative TET-ON consisting of the coding sequences for amino acids 1–207 of the tet repressor placed under the control of the pCMV promoter.
Figure 4:
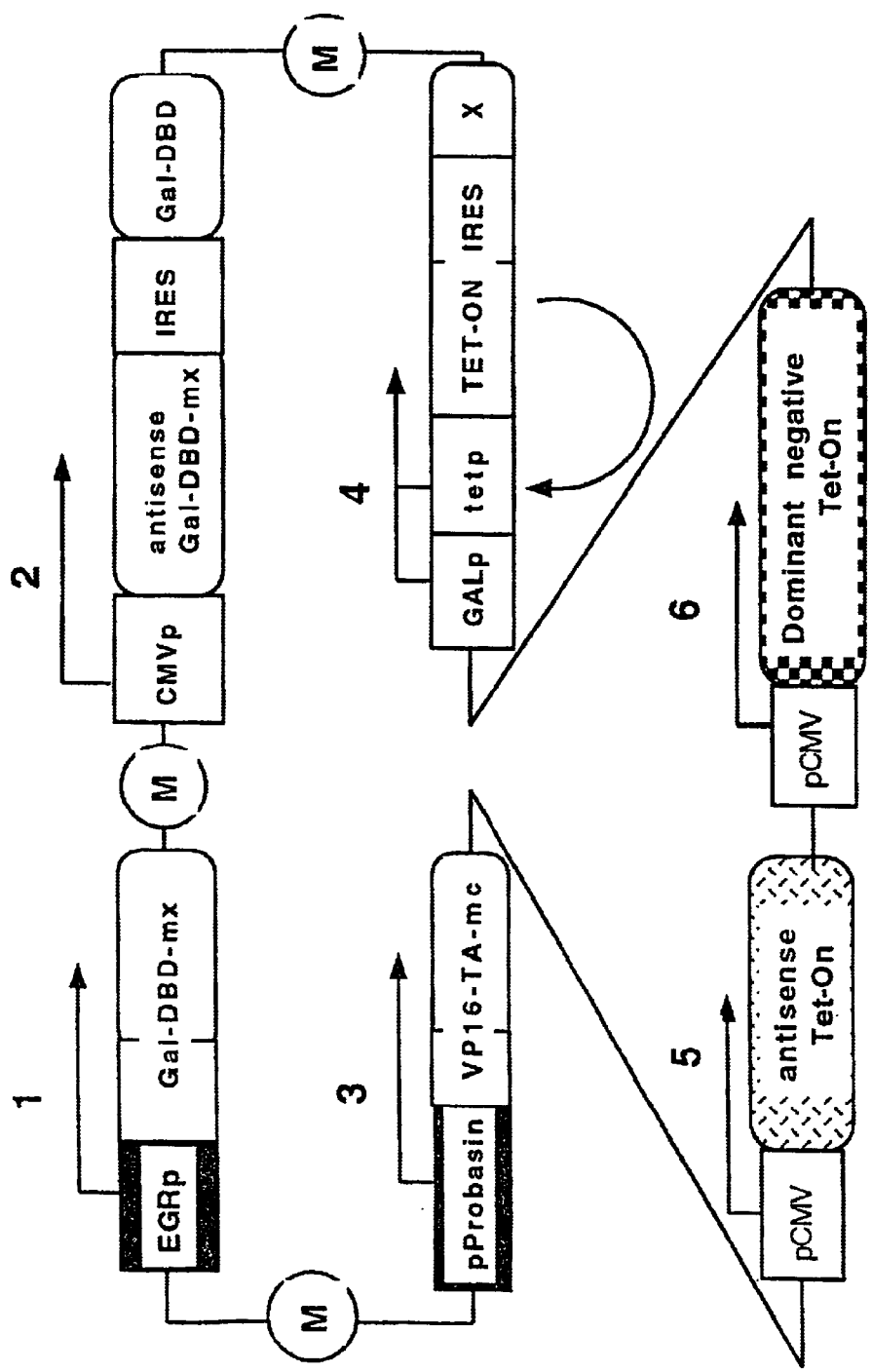
FIG. 4 shows the structure of the pRIPS-GFP (Radiation-Inducible, Prostate-specific Promoter) expression vector. The pRIPS vector is comprised of six cassettes. Gene cassette 1 differs from previously described vectors only in that it contains "Gal-DBD-mx" which is a fusion open reading frame encoding the N-terminus (amino acids 1–147) DNA-binding domain of the yeast GAL4 protein (Gal-DBD) fused to the basis helix-loop-helix-leucine zipper (bHLHLZ) domain of Max (mx, amino acids 8–112) followed by SV40 poly A. Gene cassette 2 is comprised of the minimal CMV promoter (mCMVp), "antisense Gal-DBD-mx", which is an antisense construct complementary to the Gal-DBD-mx sequence, "IRES", which is an internal ribosomal entry site and "Gal-DBD" which competes with the Gal-DBD-mx for the pGAL binding site. Gene cassette 3 is comprised of "VP16-TA-mc" which is a fusion open reading frame encoding at the N-terminus the first 11 amino acids of Gal4 (amino acids 1–147), followed by the nuclear localization signal of the SV40 large T antigen, the 130 amino acid C-terminus transactivation domain of the herpes simplex viral protein VP16, the bHLHLZ domain of c-Myc (amino acids 350–439), followed by SV40 polyA. The resulting fusion gene, VP-16TA-mc, is placed under the control of the probasin gene promoter "pProbasin" up to the first ATG. Gene cassette 4 contains "GALp", consisting of five copies of a 17-mer DNA-binding site for Gal4. The TET-ON sequence is placed under the control of the GALp-ptet promoter and the therapeutic gene, X, is linked to the TET-ON via an IRES; Gene cassette 5 contains an antisense TET-ON which is a sequence consisting of the complementary sequence to the first 80 bases of the TET-ON sequence including the ATG, placed under the control of the pCMV promoter. Gene cassette 6 contains a dominant negative TET-ON consisting of the coding sequences for amino acids 1–207 of the tet repressor placed under the control of the pCMV promoter.

Gene expression levels were optimized using a feed-forward reaction with the tetracycline-dependent transactivator, Tet-On, placed under the control of a tetracycline promoter (tetp), followed by the GAL-4 promoter (pGAL). Transient transcription initiated at pGAL leads to synthesis of a low level of Tet-On, which then binds to tetp in the presence of tetracycline. Tet-On then amplifies its own expression and that of the therapeutic gene linked to it via a feed-forward reaction. The expression of therapeutic genes is controlled by six gene cassettes in the pRIBs vector (FIG. 3). In cassette 1, the fusion gene GAL-DBD-mx (HLH-LZ domain of max fused to the DNA-binding domain of GAL-4) is regulated by EGRp. Background expression of GAL-DBD-mx is suppressed by a constitutively expressed antisense GAL-DBD-mx and a dominant negative GAL-DBD in cassette 2. In cassette 3, the transcription activation domain of the herpes simplex viral protein VP16 is fused to the HLH-LZ domain of c-Myc. The resulting fusion gene, VP16-TA-mc, placed under the control of the c-erbB-2 promoter, is expressed in breast tumor cells overexpressing c-erbB-2. GAL-DBD-mx fusion protein binds to and activates transcription from the pGAL promoter (cassette 4) by recruiting the VP16-TA-mc proteins.

In unirradiated cells, the translation of the background GAL-DBD-mx mRNA is reduced and the dominant negative GAL-DBD (without mx) competitively occupies the GALp in cassette 4, blocking Tet-On expression. Upon irradiation, GAL-DBD-mx is transiently induced 3–4 fold and temporarily overcomes the suppression by cassette 2. The GAL-DBD-mx recruits the VP-16-TA-mc (a fusion gene of the VP16 transactivation domain and the leucine zipper of myc under the control of the c-erbB-2 promoter) to the GALp and activates a low level of Tet-On transcription starting the feed-forward reaction.

In a treatment scheme using pRIBs-TNFα, for example, can be delivered systemically in a liposome complex or as a recombinant virus to tumor and normal cells alike. Without radiation and tetracycline, TNFα is not expressed. Oxytetracycline is then administered systemically followed by X-ray irradiation of known metastatic tumor sites. As a result, TNFα expression is induced in the tumor sites by the X-ray and amplified and maintained by oxytetracycline. Even though not all tumor cells may take up pRIBs-TNFα, tumor cells in the vicinity of those that do are exposed to the very high local concentration of TNFα secreted. The design of pRIBs-TNFα confers TNFα expression in the breast tumor cells only and not in the irradiated normal cells that were in the path of the X-ray. As such, systemic toxicity, if any, is limited to the low level of TNFα diffused from the tumor cells. In addition to, or instead of, TNFα, another therapeutic gene, designated X, can be used with the pRIBS vector.

Figure 5:
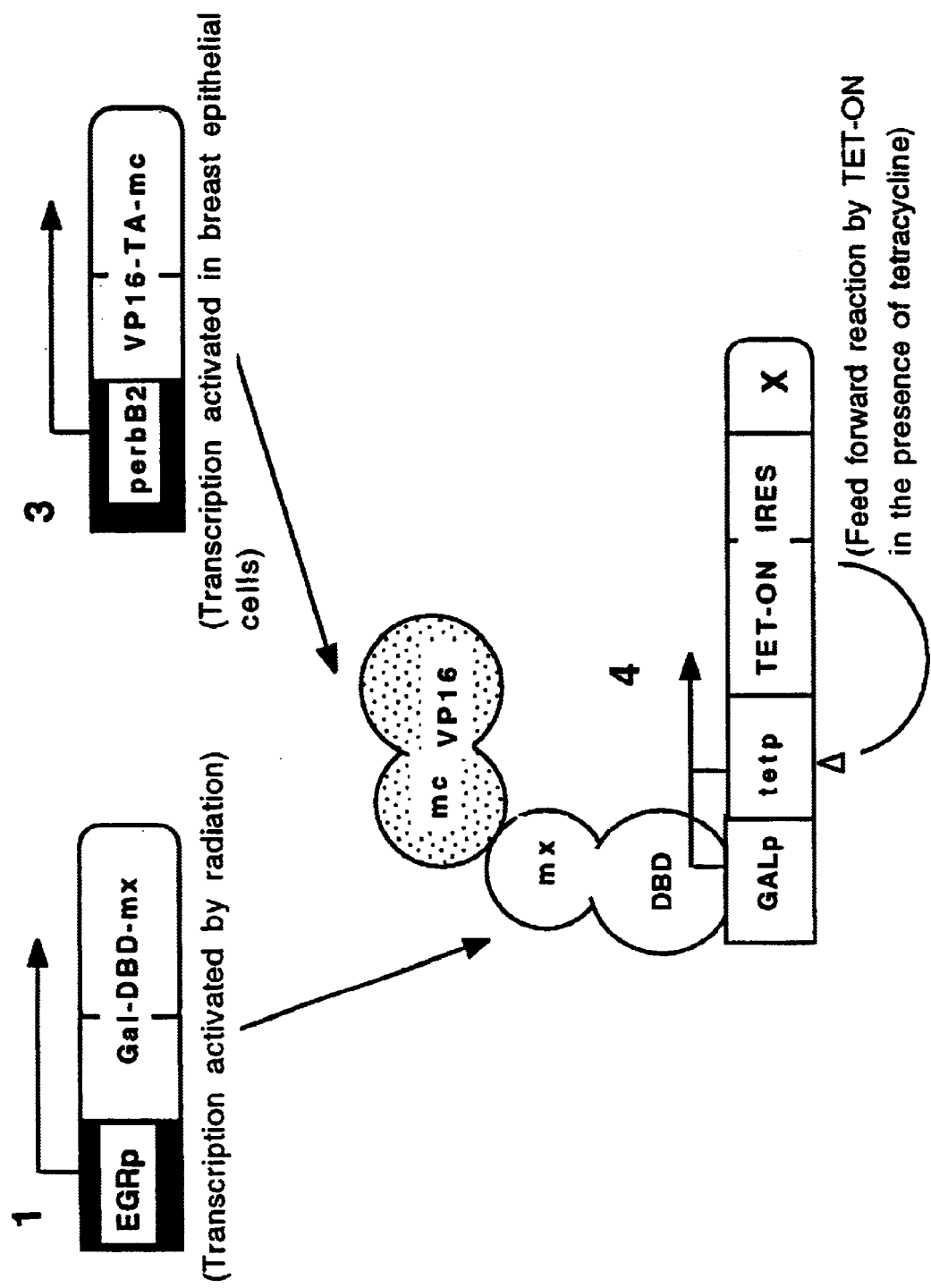
FIG. 5 is a schematic representation of the mode of action of pRIBS-GFP.
Figure 6A:
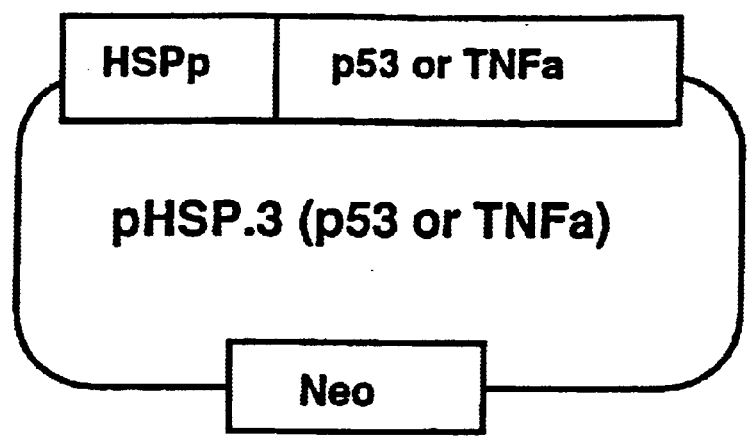
FIG. 6A shows the plasmid construct for the two genes, p53 and TNFα.
Figure 6B:
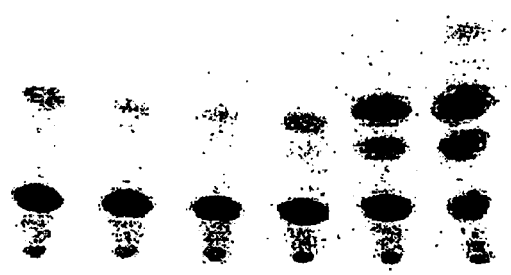
FIG. 6B depicts p53 transcriptional activity. To analyze the inducibility of the hsp promoter, the plasmid pHSP.3p53CD1 or the control pHSP.3 vector alone was cotransfected with Post-2-CAT (containing a CAT coding sequence linked to a consensus p53 binding site) into the human ovarian carcinoma cell line SKOV3 which has a homozygous deletion of p53. At 36 hours after transfection, cells were either heated or unheated. CAT activity was measured 24 hours later. Little or no activity is seen with the SKOV3 parental untransfected cells (lane 2, heated; lane 1, unheated). Similarly, with the pHSP.3 vector alone, there is no activity with or without heat (lanes 3 and 4). With the pHSP.3p53 plasmid, there is a high level of CAT activity seen at 24 hrs after heating (lane 6). However, even without heating (lane 5), there is a substantial level of p53 expression (about 25%).
Figure 7:
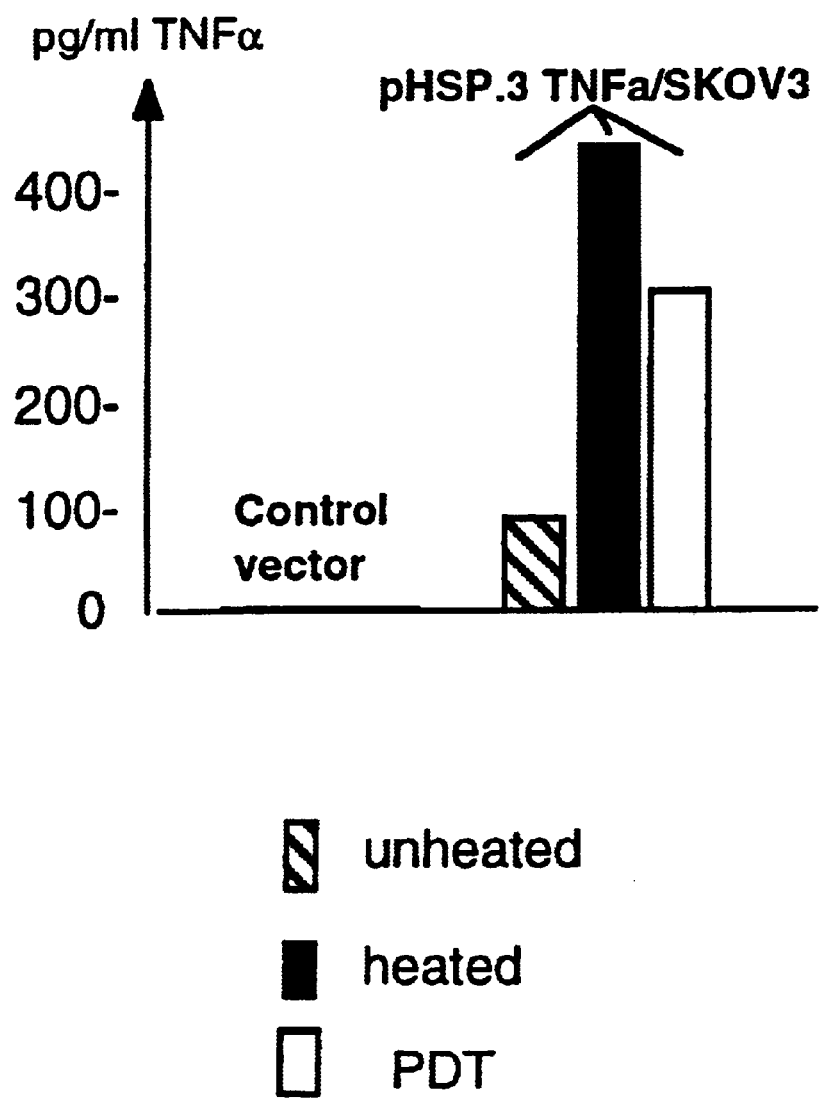
FIG. 7 depicts the induction of TNFα by heat or photodynamic therapy (PDT). The coding sequence of TNFα was subcloned into the plasmid pHSP.3 and transfected into SKOV3 cells. Stable colonies were isolated by selection in G418. Cells were either heated at 45° C. or untreated. At 6 hours after treatment, the level of TNFα in the medium was measured with a Genzyme TNFα ELISA kit. TNFα shown to be induced four-fold by heat and three-fold by PDT and secreted. However, background expression was substantial (27%).

The structure of pRIBs-GFP-1 is shown in FIG. 3 and the mode of action summarized in FIG. 5. In unirradiated cells, background GAL-DBD-mx expression and function are suppressed by cassette 2 in two ways. The antisense to GAL-DBD-mx suppresses the translation of background GAL-DBD-mx mRNA whereas the GAL-DBD protein acts as a dominant negative inhibitor by competing with GAL-DBD-mx for the pGAL promoter. In irradiated cells, GAL-DBD-mx expression is transiently induced three to 4 fold, overcoming the suppression by cassette 2. The GAL-DBD-mx recruits the VP-16-TA-mc (a fusion gene of the VP16 transactivation domain and the leucine zipper of Myc under the control of the c-erbB-2 promoter) to the GALp and activates the transient expression of the transactivator TET-ON. In the presence of tetracycline, Tet-ON is activated and it binds to and transactivates the tetp promoter (Gossen, M., et al., *Science*, 268:1766–1769 (1995)), amplifying its own level and GFP in a feed-forward reaction. Background expression of TET-ON and GFP is null in the absence of radiation or tetracycline.

EXAMPLE 7

Generation of Cell Lines and Xenografts Stably Expressing pRIBs-GFP

Two pRIBs-GFP plasmids, pRIBs-GFP-1 and pRIBs-GFP-4, with one and four copies of antisense and dominant negative gene cassettes, respectively, were constructed and stably transfected into the fibrosarcoma cell line HTB152 and the breast tumor cell lines SK-BR-3 and MDAMB231 for in vitro analysis. $5 \times 10^6$ cells are xenografted into SCID mice. While all three human cell lines form poorly differentiated tumors, only SK-BR-3 expresses a high level of c-erbB-2. Indeed, anti-erbB-2 intracellular single-chain antibody which down-regulates cell surface erbB-2, induces apoptosis only in SK-BR-3 but not MDA-MB-231 (Chumakov A. M., et al., *Oncogene* 8:3005–3011 (1993)).

The pRIBs-GFP-1 and −4 plasmids are thus used as models to optimize the conditions for testing treatment of metastatic breast tumor xenografts in nude mice with cytotoxic genes. As cytotoxic genes linked to EGRp are induced only in irradiated cells, toxicity to unirradiated cells is eliminated. However, it is important to prevent expression of cytotoxic genes in normal cells that are in the pathway of the X-ray. The three cell lines, which differ in c-erbB-2 expression, show that controlling VP16-TA-mc expression with a tissue- or tumor-specific promoter confines expression to irradiated breast tumor cells only and not the irradiated normal cells of the vital organs where the metastatic tumor cells reside.

The pRIBs-GFP plasmids are assembled as shown in FIG. 3. The. GAL-DBA-mx and the VP16-TA-mc are modified from the mammalian two hybrid system (Fearon, E. R., et al., *Proc. Natl. Acad. Sci. USA*, 89:7958–7962 (1992)). Two plasmids, pRIBs-GFP-1 and pRIBs-GFP-4, with 1 and 4 copies of antisense and dominant negative GAL-DBD driven by the minimal CMV promoter are tested.

All three cell lines are cotransfected with pRIBs-GFP and a SVneo plasmid. Cell lines stably expressing pRIBs-GFP-1 and pRIBs-GFP-4 are isolated by selection in G418. For in vivo analysis, $5 \times 10^6$ cells of each of the cell lines stably expressing the pRIBs-GFP plasmids are implanted into the flank of SCID mice (four per group) and allowed to grow to 0.5 cm in diameter. The expression of GFP in vitro and in the xenografts without radiation or oxytetracycline is analyzed by extracting the proteins into EBC buffer from the pulverized tumor and the amount of protein is quantitated by RIA.

The inducible level of GFP in vitro is measured by Western analysis and quantitated by RIA after irradiating the cells at 0–4 Gy with a Varian Clinac 2000 X-ray generator followed by administration of 0–2 μg/ml of oxytetracycline. Data using HSPp showed that the feed-forward reaction is very efficient and 0.01 μg/ml is sufficient to induce a nine-fold increase of p53 expression in 10 hours. For in vivo analysis, tumors are exposed to 0–4 Gy/X-ray. Six hours after radiation, 0–15 μg/g of oxytetracycline is injected intraperitoneally. At 3 hour intervals (for 24 hours) after an injection, tumor mass is removed and the amount of TET-ON and GFP measured relative to the total amount of actin proteins. To achieve a higher or lower level of GFP, the experiments are repeated with the level of TET-ON modified by adjusting the dose of oxytetracycline. The rate of oxytetracycline removal by excretion is monitored by analyzing plasma concentration at three hour intervals.

EXAMPLE 8

Targeting Metastatic Breast Tumors with WAPp or ST3p

The c-erbB-2 promoter had been chosen to initially validate the pRIB-X concept because human cancers overexpressing c-erbB-2 are associated with poor prognosis. It is unlikely, however, that one particular promoter will address the problem of treating different breast tumors. Therefore it is also important to target GAL-DBD-mx expression to metastatic breast tumors with the whey acidic protein promoter, WAPp (McKnight, R. A., et al., *Mol. Reprod. & Dev.*, 44:179–184 (1996)) or the stromelysin 3 promoter, ST3p (Ahmad, A., et al., Int. J. of Cancer, 73:290–296 (1997)). WAPp targets expression to breast epithelial cells while ST3p targets expression to matrix-metalloproteinase-secreting stromal cells adjacent to tumors.

pRIBs is reconstructed by replacing the c-erbB-2 promoter with either WAPp or ST3p. Breast and other tumor cell lines are screened for high and low expression of WAP and ST3. Cell lines differing in their expression of WAP and/or ST3 are used to test the expression of GFP.

The WAP promoter has been shown to be very specific for lactating mammary epithelial cells in transgenic animals (Tzeng Y J., et al., *Oncogene* 16(16):2103–2114 (1998)) and the stromelysin 3 promoter, ST3p, has been shown to be expressed only in stromal fibroblasts adjacent to cancer cells. Evidence suggests that production in stromal cell of matrix-metalloproteinases (including ST3), implicated in the process of tumor metastasis, is stimulated by the cancer cells. Thus, the targeting of VP16-TA-mc to the stromal cells will lead to the expression and release of therapeutic gene products in the vicinity of the metastatic tumor cells. It must be noted that additional treatment specificity is attained by delivering pRIBs-X with liposomes coated with antibodies to c-erbB2.

EXAMPLE 9

The Expression Vector pRIPs for Treatment of Local and Metastatic Prostate Cancer As mentioned supra, genes placed under the control of such promoters as the radiation inducible promoter of the Egr-1 gene are often expressed only transiently and at low levels. This renders them unsuitable for use in cancer therapy. To overcome these problems, the expression vector pRIPs-X (Radiation-Inducible, Prostate-specific Promoter) was designed.

The pRIPS vector is comprised of six cassettes. Gene cassette 1 differs from previously described vectors only in that it contains "Gal-DBD-mx" which is a fusion ORF encoding the N-terminus (amino acids 1–147) DNA-binding domain of the yeast GAL4 protein (Gal-DBD) fused to the basis helix-loop-helix-leucine zipper (bHLHLZ) domain of Max (mx, amino acids 8–112) followed by SV40 poly A. Gene cassette 2 is comprised of the minimal CMV promoter (mCMVp), "antisense Gal-DBD-mx", which is an antisense construct complementary to the Gal-DBD-mx sequence, "IRES", which is an internal ribosomal entry site and "Gal-DBD" which competes with the Gal-DBD-mx for the pGAL binding site. Gene cassette 3 is comprised of "VP16-TA-mc" which is a fusion ORF encoding at the N-terminus the first 11 amino acids of Gal4 (amino acids 1–147), followed by the nuclear localization signal of the SV40 large T antigen, the 130 amino acid C-terminus transactivation domain of the herpes simplex viral protein VP16, the bHLHLZ domain of c-Myc (amino acids 350–439), followed by SV40 polyA. The resulting fusion gene, VP16-TA-mc, is placed under the control of the probasin gene promoter "pProbasin" up to the first ATG. Gene cassette 4 contains "GALp", consisting of five copies of a 17-mer DNA-binding site for Gal4. The TET-ON sequence is placed under the control of the GALp-ptet promoter and the therapeutic gene, X, is linked to the TET-ON via an IRES; Gene cassette 5 contains an antisense TET-ON which is a sequence consisting of the complementary sequence to the first 80 bases of the TET-ON sequence including the ATG, placed under the control of the pCMV promoter. Gene cassette 6 contains a dominant negative TET-ON consisting of the coding sequences for amino acids 1–207 of the tet repressor placed under the control of the pCMV promoter. In other variants of pRIPs-X, pProbasin is replaced by PSA, the promoter region of the prostate specific antigen, or other prostate-specific genes.

EXAMPLE 10

The Expression Vector pHIBs-X for Treatment of Local and Metastatic Breast and Ovarian Cancer The expression vector pHIBs-X was designed and is comprised of six cassettes. Gene cassette 1 differs from previously described vectors only in that it contains "Gal-DBD-mx" which is a fusion ORF encoding the N-terminus (amino acids 1–147) DNA-binding domain of the yeast GAL4 protein (Gal-DBD) fused to the basis helix-loop-helix-leucine zipper (bHLHLZ) domain of Max (mx, amino acids 8–112) followed by SV40 poly A. The resulting fusion gene GAL-DBD-mx is controlled by the heat inducible HSP promoter. Gene cassette 2 is comprised of the minimal CMV promoter (mCMVp), "antisense Gal-DBD-mx", which is an antisense construct complementary to the Gal-DBD-mx sequence, "IRES", which is an internal ribosomal entry site and "Gal-DBD" which competes with the Gal-DBD-mx for the pGAL binding site. Gene cassette 3 is comprised of "VP16-TA-mc" which is a fusion ORF encoding at the N-terminus the first 11 amino acids of Gal4 (amino acids 1–147), followed by the nuclear localization signal of the SV40 large T antigen, the 130 amino acid C-terminus transactivation domain of the herpes simplex viral protein VP16, the bHLHLZ domain of c-Myc (amino acids 350–439), followed by SV40 polyA. The resulting fusion gene, VP-16TA-mc, is placed under the control of the c-erbB-2 promoter "perbB2" up to the first ATG. Gene cassette 4 contains "GALp", consisting of five copies of a 17-mer DNA-binding site for Gal4. The TET-ON sequence is placed under the control of the GALp-ptet promoter and the therapeutic gene, X, is linked to the TET-ON via an IRES; Gene cassette 5 contains an antisense TET-ON which is a sequence consisting of the complementary sequence to the first 80 bases of the TET-ON sequence including the ATG, placed under the control of the pCMV promoter. Gene cassette 6 contains a dominant negative TET-ON consisting of the coding sequences for amino acids 1–207 of the tet repressor placed under the control of the pCMV promoter.

The pHIBs-X expression vector is identical to the pRIBs-X plasmid except for gene cassette 1 where the Egr-1 promoter in pRIBs-X is replaced by the HSP 70 promoter. pHIBs-X specifically targets local and metastatic breast and ovarian tumors when the tumors are exposed to heat.

EXAMPLE 11

Figure 10:
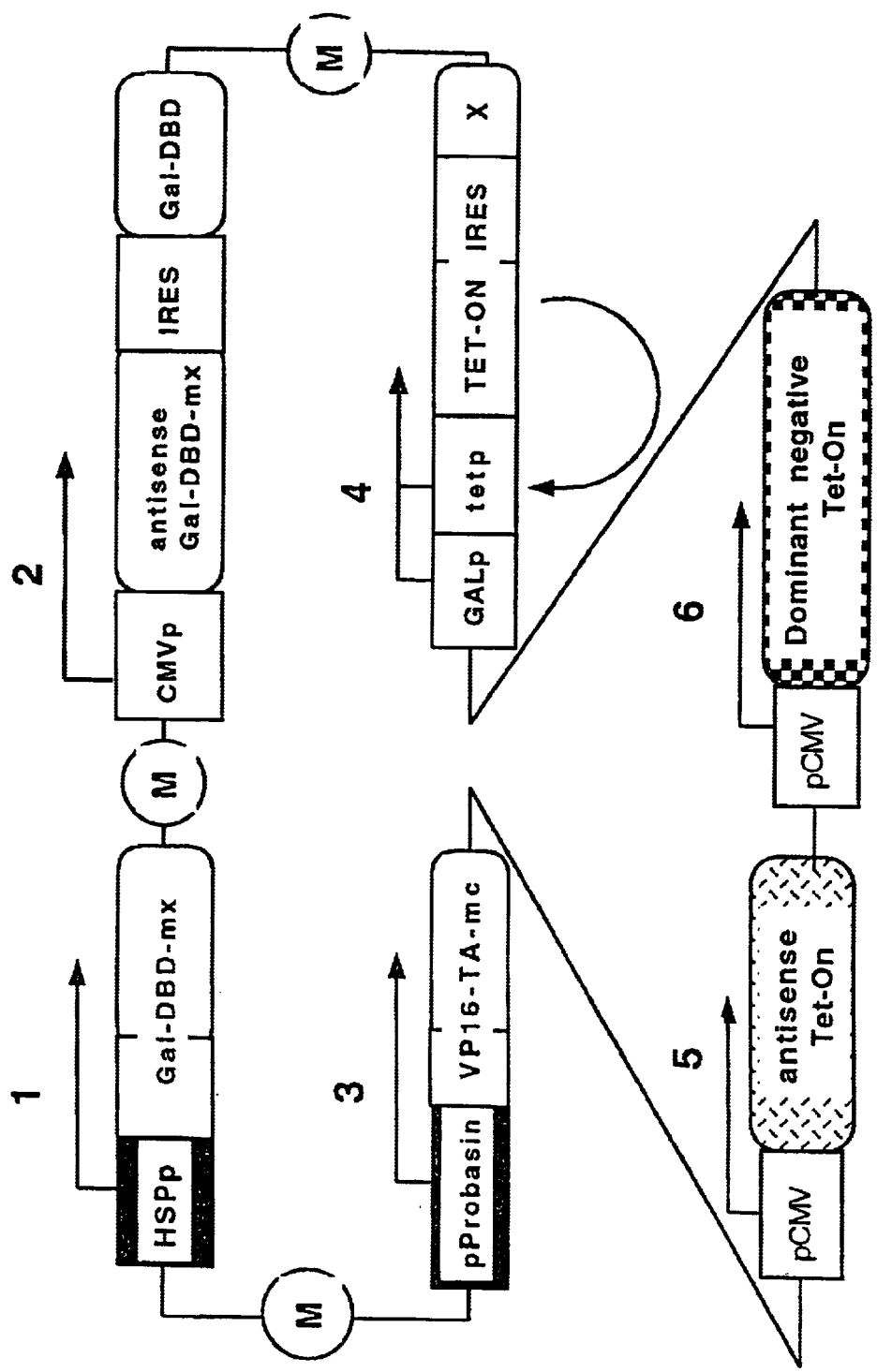
FIG. 10 illustrates the structure of the pHIPs-GFP (Heat-Inducible, Prostate-specific Promoter) expression vector. The pHIPS vector is comprised of six cassettes. Gene cassette 1 differs from previously described vectors only in that it contains "Gal-DBD-mx" which is a fusion open reading frame encoding the N-terminus (amino acids 1–147) DNA-binding domain of the yeast GAL4 protein (Gal-DBD) fused to the basis helix-loop-helix-leucine zipper (bHLHLZ) domain of Max (mx, amino acids 8–112) followed by SV40 poly A. The resulting fusion gene GAL-DBD-mx is controlled by the heat inducible HSP promoter. Gene cassette 2 is comprised of the minimal CMV promoter (mCMVp), "antisense Gal-DBD-mx", which is an antisense construct complementary to the Gal-DBD-mx sequence, "IRES", which is an internal ribosomal entry site and "Gal-DBD" which competes with the Gal-DBD-mx for the pGAL binding site. Gene cassette 3 is comprised of "VP16-TA-mc" which is a fusion open reading frame encoding at the N-terminus the first 11 amino acids of Gal4 (amino acids 1–147), followed by the nuclear localization signal of the SV40 large T antigen, the 130 amino acid C-terminus transactivation domain of the herpes simplex viral protein VP16, the bHLHLZ domain of c-Myc (amino acids 350–439), followed by SV40 polyA. The resulting fusion gene, VP16-TA-mc, is placed under the control of the probasin gene promoter (pProbasin) up to the first ATG. Gene cassette 4 contains "GALp", consisting of five copies of a 17-mer DNA-binding site for Gal4. The TET-ON sequence is placed under the control of the GALp-ptet promoter and the therapeutic gene, X, is linked to the TET-ON via an IRES; Gene cassette 5 contains an antisense TET-ON which is a sequence consisting of the complementary sequence to the first 80 bases of the TET-ON sequence including the ATG, placed under the control of the pCMV promoter. Gene cassette 6 contains a dominant negative TET-ON consisting of the coding sequences for amino acids 1–207 of the tet repressor placed under the control of the pCMV promoter.

The Expression Vector pHIPs-X for Treatment of Local and Metastatic Prostate Cancer FIG. 10 illustrates the structure of the pHIPs-GFP (Heat-Inducible, Prostate-specific Promoter) expression vector. This vector is comprised of six cassettes. Gene cassette 1 differs from previously described vectors only in that it contains "Gal-DBD-mx" which is a fusion ORF encoding the N-terminus (amino acids 1–147) DNA-binding domain of the yeast GAL4 protein (Gal-DBD) fused to the basis helix-loop-helix-leucine zipper (bHLHLZ) domain of Max (mx, amino acids 8–112) followed by SV40 poly A. The resulting fusion gene GAL-DBD-mx is controlled by the heat inducible HSP promoter. Gene cassette 2 is comprised of the minimal CMV promoter (mCMVp), "antisense Gal-DBD-mx", which is an antisense construct complementary to the Gal-DBD-mx sequence, "IRES", which is an internal ribosomal entry site and "Gal-DBD" which competes with the Gal-DBD-mx for the pGAL binding site. Gene cassette 3 is comprised of "VP16-TA-mc" which is a fusion ORF encoding at the N-terminus the first 11 amino acids of Gal4 (amino acids 1–147), followed by the nuclear localization signal of the SV40 large T antigen, the 130 amino acid C-terminus transactivation domain of the herpes simplex viral protein VP16, the bHLHLZ domain of c-Myc (amino acids 350–439), followed by SV40 polyA. The resulting fusion gene, VP16-TA-mc, is placed under the control of the probasin gene promoter (pProbasin) up to the first ATG. Gene cassette 4 contains "GALp", consisting of five copies of a 17-mer DNA-binding site for Gal4. The TET-ON sequence is placed under the control of the GALp-ptet promoter and the therapeutic gene, X, is linked to the TET-ON via an IRES; Gene cassette 5 contains an antisense TET-ON which is a sequence consisting of the complementary sequence to the first 80 bases of the TET-ON sequence including the ATG, placed under the control of the pCMV promoter. Gene cassette 6 contains a dominant negative TET-ON consisting of the coding sequences for amino acids 1–207 of the tet repressor placed under the control of the pCMV promoter.

The pHIPs-X expression vector is identical to the pRIPs-X plasmid except for gene cassette 1 where the Egr-1 promoter in pRIBs-X and pRIPs-X is replaced by the HSP 70 promoter. pHIPs-X specifically targets local and metastatic prostate tumors when the tumors are exposed to heat.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A recombinant vector, pDATH-X (Dominant negative, Antisense, TET-ON controllable Heat shock promoter plasmid), said vector comprises:
- (a) cassette 1 comprising TET-ON expressed under the control of a heat shock promoter and a tet operator, wherein said TET-ON consists of a fusion of the coding sequences for amino acids 1–207 (SEQ ID NO:1) of tetracycline repressor and the C-terminus transcription activation domain (SEQ ID NO:2) of VP16 protein of the herpes simplex virus, wherein said heat shock promoter consists of heat shock response elements of the human heat shock 70 gene promoter (SEQ ID NO:3) linked to a minimal cytomegalovirus promoter (pCMV) and wherein said tet operator consists of 19 bp inverted repeats (SEQ ID NO:4) of operator O2 of TN10 to which tet repressor and TET-ON bind;
- (b) cassette 2 comprising a cloning site for a therapeutic gene X downstream of a tetp-CMV promoter consisting of a tet operator linked to a minimal cytomegalovirus promoter (pCMV), wherein said tet operator consists of 19 bp inverted repeats (SEQ ID NO:4) of operator O2 of TN10 to which tet repressor and TET-ON bind;
- (c) cassette 3 comprising antisense TET-ON under the control of pCMV promoter, wherein said antisense TET-ON consists of an antisense sequence complementary to the first 80 nucleotides encoding the TET-ON sequence of (a) above, beginning with the ATG start codon; and,
- (d) cassette 4 comprising a dominant negative TET-ON under the control of pCMV promoter, wherein said dominant negative TET-ON consists of tet repressor without a VP16 transactivation domain.

2. The recombinant vector of claim 1, wherein said therapeutic gene X is TNF-α, and said vector has the sequence of SEQ ID NO:5.

* * * * *

SEQUENCE LISTING

<160> NUMBER OF SEQ ID NOS: 5

<210> SEQ ID NO 1
<211> LENGTH: 207
<212> TYPE: PRT
<213> ORGANISM: Unknown
<220> FEATURE:
<221> NAME/KEY: CHAIN
<223> OTHER INFORMATION: amino acids 1-207 of tetracycline repressor

<400> SEQUENCE: 1

-continued

```
Met Ser Arg Leu Asp Lys Ser Lys Val Ile Asn Ser Ala Leu Glu
                 5                  10                  15

Leu Leu Asn Glu Val Gly Ile Glu Gly Leu Thr Thr Arg Lys Leu
             20                  25                  30

Ala Gln Lys Leu Gly Val Glu Gln Pro Thr Leu Tyr Trp His Val
             35                  40                  45

Lys Asn Lys Arg Ala Leu Leu Asp Ala Leu Ala Ile Glu Met Leu
             50                  55                  60

Asp Arg His His Thr His Phe Cys Pro Leu Lys Gly Glu Ser Trp
             65                  70                  75

Gln Asp Phe Leu Arg Asn Asn Ala Lys Ser Phe Arg Cys Ala Leu
             80                  85                  90

Leu Ser His Arg Asn Gly Ala Lys Val His Ser Asp Thr Arg Pro
             95                 100                 105

Thr Glu Lys Gln Tyr Glu Thr Leu Glu Asn Gln Leu Ala Phe Leu
            110                 115                 120

Cys Gln Gln Gly Phe Ser Leu Glu Asn Ala Leu Tyr Ala Leu Ser
            125                 130                 135

Ala Val Gly His Phe Thr Leu Gly Cys Val Leu Glu Asp Gln Glu
            140                 145                 150

His Gln Val Ala Lys Glu Glu Arg Glu Thr Pro Thr Thr Asp Ser
            155                 160                 165

Met Pro Pro Leu Leu Arg Gln Ala Ile Glu Leu Phe Asp His Gln
            170                 175                 180

Gly Ala Glu Pro Ala Phe Leu Phe Gly Leu Glu Leu Ile Ile Cys
            185                 190                 195

Gly Leu Glu Lys Gln Leu Lys Cys Glu Ser Gly Ser
            200                 205
```

<210> SEQ ID NO 2
<211> LENGTH: 128
<212> TYPE: PRT
<213> ORGANISM: Unknown
<220> FEATURE:
<221> NAME/KEY: CHAIN
<223> OTHER INFORMATION: C-terminal last 128 amino acids of the
      transcription activation domain of VP16
      of the herpes simplex virus

<400> SEQUENCE: 2

```
Ala Tyr Ser Arg Ala Arg Thr Lys Asn Asn Tyr Gly Ser Thr Ile
                 5                  10                  15

Glu Gly Leu Leu Asp Leu Pro Asp Asp Ala Pro Glu Glu Ala
             20                  25                  30

Gly Leu Ala Ala Pro Arg Leu Ser Phe Leu Pro Ala Gly His Thr
             35                  40                  45

Arg Arg Leu Ser Thr Ala Pro Pro Thr Asp Val Ser Leu Gly Asp
             50                  55                  60

Glu Leu His Leu Asp Gly Glu Asp Val Ala Met Ala His Ala Asp
             65                  70                  75

Ala Leu Asp Asp Phe Asp Leu Asp Met Leu Gly Asp Gly Asp Ser
             80                  85                  90

Pro Gly Pro Gly Phe Thr Pro His Asp Ser Ala Pro Tyr Gly Ala
             95                 100                 105

Leu Asp Met Ala Asp Phe Glu Phe Glu Gln Met Phe Thr Asp Ala
            110                 115                 120
```

```
Leu Gly Ile Asp Glu Tyr Gly Gly
            125

<210> SEQ ID NO 3
<211> LENGTH: 222
<212> TYPE: DNA
<213> ORGANISM: Unknown
<220> FEATURE:
<221> NAME/KEY: gene
<223> OTHER INFORMATION: heat shock response element of human heat shock
      70 gene promoter

<400> SEQUENCE: 3
cccgggcggg cgggcgggag gctctcgact gggcgggaag gtgcgggaag         50
gttcgcggcg gcggggtcgg ggaggtgcaa aaggatgaaa agcccgtgga        100
cggagctgag cagatccggc cgggctggcg gcagagaaac cgcagggaga        150
gcctcactgc tgagcgcccc tcgacgcggg cggcagcagc ctccgtggcc        200
tccagcatcc gacaagaagc tt                                      222

<210> SEQ ID NO 4
<211> LENGTH: 19
<212> TYPE: DNA
<213> ORGANISM: Unknown
<220> FEATURE:
<221> NAME/KEY: gene
<223> OTHER INFORMATION: 19-base pair inverted repeats of operator
      O2 of TN10

<400> SEQUENCE: 4
tccctatcag tgatagaga                                           19

<210> SEQ ID NO 5
<211> LENGTH: 10728
<212> TYPE: DNA
<213> ORGANISM: Unknown
<220> FEATURE:
<221> NAME/KEY: misc_feature
<223> OTHER INFORMATION: recombinant vector pDATH-TNFα

<400> SEQUENCE: 5
tcgagcccgg gcgggcgggc gggaggctct cgactgggcg ggaaggtgcg         50
ggaaggttcg cggcggcggg gtcggggagg tgcaaaagga tgaaaagccc        100
gtggacggag ctgagcagat ccggccgggc tggcggcaga gaaaccgcag        150
ggagagcctc actgctgagc gccccctcgac gcggcggca gcagcctccg        200 tggcctccag catccgacaa gaagcttgtc gagtttacca ctccctatca        250
gtgatagaga aaagtgaaag tcgagtttac cactccctat cagtgataga        300
gaaaagtgaa agtcgagttt accactccct atcagtgata gagaaaagtg        350
aaagtcgagt ttaccactcc ctatcagtga tagagaaaag tgaaagtcga        400
gtttaccact ccctatcagt gatagagaaa agtgaaagtc gagtttacca        450
ctccctatca gtgatagaga aaagtgaaag tcgagtttac cactccctat        500
cagtgataga gaaaagtgaa agtcgagctc ggtacccggg tcgagtaggc        550
gtgtacggtg ggaggcctat ataagcagag ctcgtttagt gaaccgtcag        600
atcgcctgga gacgccatcc acgctgtttt gacctccata agagcaccg         650 ggaccgatcc agcctccgcg gccccgaatt catatgtcta gattagataa        700
```

-continued

| | |
|---|---|
| aagtaaagtg attaacagcg cattagagct gcttaatgag gtcggaatcg | 750 |
| aaggtttaac aacccgtaaa ctcgcccaga agcttggtgt agagcagcct | 800 |
| acactgtatt ggcatgtaaa aaataagcgg gctttgctcg acgccttagc | 850 |
| cattgagatg ttagataggc accatactca cttttgccct ttaaaagggg | 900 |
| aaagctggca agattttta cgcaataacg ctaaaagttt tagatgtgct | 950 |
| ttactaagtc atcgcaatgg agcaaaagta cattcagata cacggcctac | 1000 |
| agaaaaacag tatgaaactc tcgaaaatca attagccttt ttatgccaac | 1050 |
| aaggtttttc actagagaac gcgttatatg cactcagcgc tgtggggcat | 1100 |
| tttactttag gttgcgtatt ggaagatcaa gagcatcaag tcgctaaaga | 1150 |
| agaaagggaa acacctacta ctgatagtat gccgccatta ttacgacaag | 1200 |
| ctatcgaatt atttgatcac caaggtgcag agccagcctt cttattcggc | 1250 |
| cttgaattga tcatatgcgg attagaaaaa caacttaaat gtgaaagtgg | 1300 |
| gtccgcgtac agccgcgcgc gtacgaaaaa caattacggg tctaccatcg | 1350 |
| agggcctgct cgatctcccg gacgacgacg ccccgaaga ggcggggctg | 1400 |
| gcggctccgc gcctgtcctt tctccccgcg ggacacacgc gcagactgtc | 1450 |
| gacgccccc ccgaccgatg tcagcctggg ggacgagctc cacttagacg | 1500 |
| gcgaggacgt ggcgatggcg catgccgacg cgctagacga tttcgatctg | 1550 |
| gacatgttgg gggacgggga ttccccgggt ccgggattta cccccacga | 1600 |
| ctccgccccc tacggcgctc tggatatggc cgacttcgag tttgagcaga | 1650 |
| tgtttaccga tgcccttgga attgacgagt acggtgggta gggggcgcga | 1700 |
| ggatccagac atgataagat acattgatga gtttggacaa accacaacta | 1750 |
| gaatgcagtg aaaaaaatgc tttatttgtg aaatttgtga tgctattgct | 1800 |
| ttatttgtaa ccattataag ctgcaataaa caagttaaca acaacaattg | 1850 |
| cattcatttt atgtttcagg ttcagggggga ggtgtgggag gttttttaaa | 1900 |
| gcaagtaaaa cctctacaaa tgtggtatgg ctgattatga tcctgcaagc | 1950 |
| ctcgtcgtct ggccggacca cgctatctgt gcaaggtccc cggacgcgcg | 2000 |
| ctccatgagc agagcgcccg ccgccgaggc aagactcggg cggcgccctg | 2050 |
| cccgtcccac caggtcaaca ggcggtaacc ggcctcttca tcgggaatgc | 2100 |
| gcgcgacctt cagcatcgcc ggcatgtccc ctggcggacg ggaagtatca | 2150 |
| gctcgaccaa gcttggcgag attttcagga gctaaggaag ctaaaatgga | 2200 |
| gaaaaaatc actggatata ccaccgttga tatatcccaa tggcatcgta | 2250 |
| aagaacattt tgaggcattt cagtcagttg ctcaatgtac ctataaccag | 2300 |
| accgttcagc tctagagcaa ttcctttgcc taatttaaat gaggacttaa | 2350 |
| cctgtggaaa tattttgatg tgggaagctg ttactgttaa aactgaggtt | 2400 |
| attggggtaa ctgctatgtt aaacttgcat tcagggacaa aaaaaactca | 2450 |
| tgaaaatggt gctggaaaac ccattcaagg gtcaaatttt cattttttg | 2500 |
| ctgttggtgg ggaacctttg gagctgcagg gtgtgttagc aaactacagg | 2550 |
| accaaatatc ctgctcaaac tgtaacccca aaaaatgcta cagttgacag | 2600 |
| tcagcagatg aacactgacc acaaggctgt tttggataag gataatgctt | 2650 |
| atccagtgga gtgctgggtt cctgatccaa gtaaaaatga aaacactaga | 2700 |

-continued

```
tattttggaa cctacacagg tggggaaaat gtgcctcctg ttttgcacat      2750
tactaacaca gcaaccacag tgcttcttga tgagcagggt gttgggccct      2800
tgtgcaaagc tgacagcttg tatgtttctg ctgttgacat tgtgggctg       2850
tttaccaaca cttctggaac acagcagtgg aagggacttc ccagatattt      2900
taaaattacc cttagaaagc ggtctgtgaa aaaccctac ccaatttcct       2950
ttttgttaag tgacctaatt aacaggagga cacagagggt ggatgggcag      3000
cctatgattg gaatgtcctc tcaagtagag gaggttaggg tttatgagga      3050
cacagaggag cttcctgggg atccagacat gataagatac attgatgagt      3100
ttggacaaac acaactaga atgcagtgaa aaaaatgctt tatttgtgaa       3150
atttgtgatg ctattgcttt atttgtaacc attataagct gcaataaaca      3200
agttaacaac aacaattgca ttcattttat gtttcaggtt caggggggagg     3250
tgtgggaggt tttttaaagc aagtaaaacc tctacaaatg tggtatggct      3300
gattatgatc tctagtcaag gcactataca tcaaatattc cttattaacc      3350
cctttacaaa ttaaaaagct aaggtacac aatttttgag catagttatt       3400
aatagcagac actctatgcc tgtgtggagt aagaaaaaac agtatgttat      3450
gattataact gttatgccta cttataaagg ttacagaata ttttttccata     3500
attttcttgt atagcagtgc agcttttttcc tttgtggtgt aaatagcaaa     3550
gcaagcaaga gttctattac taaacacagc atgactcaaa aaacttagca     3600
attctgaagg aaagtccttg ggtcttcta cctttctctt ctttttttgga      3650
ggagtagaat gttgagagtc agcagtagcc tcatcatcac tagatggcat      3700
ttcttctgag caaaacaggt tttcctcatt aaaggcattc caccactgct      3750
cccattcatc agttccatag gttggaatct aaaatacaca aacaattaga      3800
atcagtagtt taacacatta tacacttaaa aattttatat ttaccttaga      3850
gctttaaatc tctgtaggta gttttgtccaa ttatgtcaca ccacagaagt     3900
aaggttcctt cacaaagatc cgcctccggc gaatttctgc cattcatccg      3950
cttattatca cttattcagg cgtagcacca ggcgtttaag ggcaccaata      4000
actgccttaa aaaaattacg ccccgccctg ccactcatcg cagtgctcta      4050
gaactagtgg atccccggg ctgcaggaat tcgatatcaa gcttatcgat       4100
accgtcgaga tccctgcag cattctggcc agaaccaaag gctccctggt       4150
ctccagattc cagatgtcag ggatcaaagc tgtaggcccc agtgagttct      4200
ggaggcccca gtttgaattc ttagtggttg ccagcacttc actgtgcagg      4250
ccacacattc ctgaatccca ggtttcgaag tggtggtctt gttgcttaaa      4300
gttctaagct tgggttccga ccctaagccc ccaattctct ttttgagcca      4350
gaagaggttg agggtgtctg aaggaggggg taataaaggg attggggcag      4400
gggaggcgtt tgggaaggtt ggatgttcgt cctcctcaca gggcaatgat      4450
cccaaagtag acctgcccag actcggcaaa gtcgagatag tcgggccgat      4500
tgatctcagc gctgagtcgg tcacccttct ccagctggaa gacccctccc      4550
agatagatgg gctcatacca gggcttggcc tcagcccct ctgggtctc        4600
cctctggcag gggctcttga tggcagagag gaggttgacc ttggtctggt      4650
```

```
aggagacggc gatgcggctg atggtgtggg tgaggagcac atgggtggag       4700
gggcagcctt ggcccttgaa gaggacctgg gagtagatga ggtacaggcc       4750
ctctgatggc accaccagct ggttatctct cagctccacg ccattggcca       4800
ggagggcatt ggcccggcgg ttcagccact ggagctgccc ctcagcttga       4850
gggtttgcta caacatgggc tacaggcttg tcactcgggg ttcgagaaga       4900
tgatctgact gcctgggcca gagggctgat tagagagagg tccctggggg       4950
actcttccct ctgggggccg atcactccaa agtgcagcag gcagaagagc       5000
gtggtggcgc ctgccacgat caggaaggag aagaggctga ggaacaagca       5050
ccgcctggag ccctgggggcc cccctgtctt cttggggagc gcctcctcgg      5100
ccagctccac gtcccggatc atgctttcag tgctcatggt gtcctttcca       5150
ggggagagag ggtggagccg tgggtcagta tgtgagagga agagaacctg       5200
cctggcagct tgtcagggtg tgctgcaggg atctcgacct cgactctaga       5250
ggatccccgg gtaccgagct cgaattcggg gccgcggagg ctggatcggt       5300
cccggtgtct tctatggagg tcaaaacagc gtggatggcg tctccaggcg       5350
atctgacggt tcactaaacg agctctgctt ataggcct cccaccgtac         5400
acgcctactc gacccgggta ccgagctcga ctttcacttt tctctatcac       5450
tgatagggag tggtaaactc gactttcact tttctctatc actgataggg       5500
agtggtaaac tcgactttca cttttctcta tcactgatag ggagtggtaa       5550
actcgacttt cacttttctc tatcactgat agggagtggt aaactcgact       5600
ttcacttttc tctatcactg atagggagtg gtaaactcga cttttcacttt      5650
tctctatcac tgatagggag tggtaaactc gactttcact tttctctatc       5700
actgataggg agtggtaaac tcgatcgagg ggggcccgg tacccagctt        5750
ttgttccctt tagtgagggt taattgcgcg cttggcgtaa tcatggtcat       5800
agctgtttcc tgtgtgaaat tgttatccgc tgcattaatg aatcggccaa       5850
cgcgcgggga gaggcggttt gcgtattggg cgctcttccg cttcctcgct       5900
cactgactcg ctgcgctcgg tcgttcggct gcggcgagcg gtatcagctc       5950
actcaaaggc ggtaatacgg ttatccacag aatcagggga taacgcagga       6000
aagaacatgt gagcaaaagg ccagcaaaag gccaggaacc gtaaaaaggc       6050
cgcgttgctg gcgtttttcc ataggctccg ccccctgac gagcatcaca       6100
aaaatcgacg ctcaagtcag aggtggcgaa acccgacagg actataaaga       6150
taccaggcgt ttccccctgg aagctccctc gtgcgctctc ctgttccgac       6200
cctgccgctt accggatacc tgtccgcctt tctcccttcg ggaagcgtgg       6250
cgctttctca atgctcacgc tgtaggtatc tcagttcggt gtaggtcgtt       6300
cgctccaagc tgggctgtgt gcacgaaccc cccgttcagc ccgaccgctg       6350
cgccttatcc ggtaactatc gtcttgagtc aacccggta agacacgact        6400
tatcgccact ggcagcagcc actggtaaca ggattagcag agcgaggtat       6450
gtaggcggtg ctacagagtt cttgaagtgg tggcctaact acggctacac       6500
tagaaggaca gtatttggta tctgcgctct gctgaagcca gttaccttcg       6550
gaaaaagagt tggtagctct tgatccggca aacaaaccac cgctggtagc       6600
ggtggttttt ttgtttgcaa gcagcagatt acgcgcagaa aaaaaggatc       6650
```

-continued

```
tcaagaagat cctttgatct tttctacggg gtctgacgct cagtggaacg      6700
aaaactcacg ttaagggatt ttggtcatga gattatcaaa aaggatcttc      6750
acctagatcc ttttaaatta aaaatgaagt tttaaatcaa tctaaagtat      6800
atatgagtaa acttggtctg acagttacca atgcttaatc agtgaggcac      6850
ctatctcagc gatctgtcta tttcgttcat ccatagttgc ctgactcccc      6900
gtcgtgtaga taactacgat acgggagggc ttaccatctg gccccagtgc      6950
tgcaatgata ccgcgagacc cacgctcacc ggctccagat ttatcagcaa      7000
taaaccagcc agccggaagg gccgagcgca gaagtggtcc tgcaacttta      7050
tccgcctcca tccagtctat taattgttgc cgggaagcta gagtaagtag      7100
ttcgccagtt aatagtttgc gcaacgttgt tgccattgct acaggcatcg      7150
tggtgtcacg ctcgtcgttt ggtatggctt cattcagctc cggttcccaa      7200
cgatcaaggc gagttacatg atcccccatg ttgtgcaaaa aagcggttag      7250
ctccttcggt cctccgatcg ttgtcagaag taagttggcc gcagtgttat      7300
cactcatggt tatggcagca ctgcataatt ctcttactgt catgccatcc      7350
gtaagatgct tttctgtgac tggtgagtac tcaaccaagt cattctgaga      7400
atagtgtatg cggcgaccga gttgctcttg cccggcgtca atacgggata      7450
ataccgcgcc acatagcaga actttaaaag tgctcatcat tggaaaacgt      7500
tcttcggggc gaaaactctc aaggatctta ccgctgttga gatccagttc      7550
gatgtaaccc actcgtgcac ccaactgatc ttcagcatct tttactttca      7600
ccagcgtttc tgggtgagca aaaacaggaa ggcaaaatgc cgcaaaaaag      7650
ggaataaggg cgacacggaa atgttgaata ctcatactct tcctttttca      7700
atctgaacgt tctggttata ggtacattga gcaactgact gaaatgcctc      7750
aaaatgttct ttacgatgcc attgggatat atcaacggtg gtatatccag      7800
tgatttttttt ctccattttta gcttccttag ctcctgaaaa tctcgccaag     7850
cttggtcgag ctgatacttc ccgtccgcca ggggacatgc cggcgatgct      7900
gaaggtcgcg cgcattcccg atgaagaggc cggttaccgc ctgttgacct      7950
ggtgggacgg gcagggcgcc gcccgagtct tgcctcggcg gcgggcgctc      8000
tgctcatgga gcgcgcgtcc ggggaccttg cacagatagc gtggtccggc      8050
cagacgacga ggcttgcagg atcataatca gccataccac atttgtagag      8100
gttttacttg ctttaaaaaa cctcccacac ctccccctga acctgaaaca      8150
taaaatgaat gcaattgttg ttgttaactt gtttattgca gcttataatg      8200
gttacaaata aagcaatagc atcacaaatt tcacaaataa agcatttttt      8250
tcactgcatt ctagttgtgg tttgtccaaa ctcatcaatg tatcttatca      8300
tgtctggatc tcgacagtct gcgcgtgtgt cccgcgggga gaaggacag      8350
gcgcggagcc gccagccccg cctcttcggg ggcgtcgtcg tccgggagat      8400
cgagcaggcc ctcgatggta gacccgtaat tgttttttcgt acgcgcgcgg     8450
ctgtacgcgg acccactttc acatttaagt tgttttttcta atccgcatat      8500
gatcaattca aggccgaata agaaggctgg ctctgcacct tggtgatcaa      8550
ataattcgat agcttgtcgt aataatggcg gcatactatc agtagtaggt      8600
```

-continued

| | |
|---|---|
| gtttcccttt cttctttagc gacttgatgc tcttgatctt ccaatacgca | 8650 |
| acctaaagta aaatgcccca cagcgctgag tgcatataac gcgttctcta | 8700 |
| gtgaaaaacc ttgttggcat aaaaaggcta attgattttc gagagtttca | 8750 |
| tactgttttt ctgtaggccg tgtatctgaa tgtacttttg ctccattgcg | 8800 |
| atgacttagt aaagcacatc taaaacttttt agcgttattg cgtaaaaaat | 8850 |
| cttgccagct ttccccttttt aaagggcaaa agtgagtatg gtgcctatct | 8900 |
| aacatctcaa tggctaaggc gtcgagcaaa gcccgcttat tttttacatg | 8950 |
| ccaatacagt gtaggctgct ctacaccaag cttctgggcg agtttacggg | 9000 |
| ttgttaaacc ttcgattccg acctcattaa gcagctctaa tgcgctgtta | 9050 |
| atcactttac ttttatctaa tctagacata tgaattcggg gccgcggagg | 9100 |
| ctggatcggt cccggtgtct tctatggagg tcaaaacagc gtggatggcg | 9150 |
| tctccaggcg atctgacggt tcactaaacg agctctgctt atatagacct | 9200 |
| cccaccgtac acgcctaccg cccatttgcg tcaatggggc ggagttgtta | 9250 |
| cgacattttg gaaagtcccg ttgattttgg tgccaaaaca aactcccatt | 9300 |
| gacgtcaatg gggtggagac ttggaaatcc ccgtgagtca aaccgctatc | 9350 |
| cacgcccatt gatgtactgc caaaaccgca tcaccatggt aatagcgatg | 9400 |
| actaatacgt agatgtactg ccaagtagga aagtcccata aggtcatgta | 9450 |
| ctgggcataa tgccaggcgg gccatttacc gtcattgacg tcaataggg | 9500 |
| gcgtacttgg catatgatac acttgatgta ctgccaagtg ggcagtttag | 9550 |
| cgtaaatact ccacccattg acgtcaatgg aaagtcccta ttggcgttac | 9600 |
| tatgggaaca tacgtcatta ttgacgtcaa tgggcggggg tcgttgggcg | 9650 |
| gtcagccagg cgggccattt accgtaagtt atgtaacgcg gaactccata | 9700 |
| tatgggctat gaactaatga ccccgtaatt gattactatt aataactagt | 9750 |
| caataatcaa tgtcaacatg gcggtaatgt tggacatgag ccaatataaa | 9800 |
| tgtacatatt atgatatgga tacaacgtat gcaatgggcc aagctctcga | 9850 |
| cttgttttatt gcattacata tgtctagatt agataaaagt aaagtgatta | 9900 |
| acagcgcatt agagctgctt aatgaggtcg gaatcgaagg taagcttcat | 9950 |
| atgaattccg gggccgcgga ggctggatcg gtcccggtgt cttctatgga | 10000 |
| ggtcaaaaca gcgtggatgg cgtctccagg cgatctgacg gttcactaaa | 10050 |
| cgagctctgc ttatatagac ctcccaccgt acacgcctac cgcccatttg | 10100 |
| cgtcaatggg gcggagttgt tacgacattt tggaaagtcc cgttgatttt | 10150 |
| ggtgccaaaa caaactccca ttgacgtcaa tggggtggag acttggaaat | 10200 |
| ccccgtgagt caaaccgcta tccacgccca ttgatgtact gccaaaaccg | 10250 |
| catcaccatg gtaatagcga tgactaatac gtagatgtac tgccaagtag | 10300 |
| gaaagtccca taaggtcatg tactgggcat aatgccaggc gggccattta | 10350 |
| ccgtcattga cgtcaatagg gggcgtactt ggcatatgat acacttgatg | 10400 |
| tactgccaag tgggcagttt agcgtaaata ctccacccat tgacgtcaat | 10450 |
| ggaaagtccc tattggcgtt actatgggaa catacgtcat tattgacgtc | 10500 |
| aatgggcggg ggtcgttggg cggtcagcca ggcgggccat ttaccgtaag | 10550 |
| ttatgtaacg cggaactcca tatatgggct atgaactaat gaccccgtaa | 10600 |

```
ttgattacta ttaataacta gtcaataatc aatgtcaaca tggcggtaat           10650
gttggacatg agccaatata aatgtacata ttatgatatg gatacaacgt           10700
atgcaatggg ccaagctcct cgactcga                                   10728
```